US011766007B2

(12) United States Patent
Brevis Acuna

(10) Patent No.: US 11,766,007 B2
(45) Date of Patent: Sep. 26, 2023

(54) ONION VARIETY NUN 07212 ONL

(71) Applicant: NUNHEMS B.V., Nunhem (NL)

(72) Inventor: Juan Carlos Brevis Acuna, Brooks, OR (US)

(73) Assignee: Nunhems B.V., Nunhem (NL)

( * ) Notice: Subject to any disclaimer, the term of this patent is extended or adjusted under 35 U.S.C. 154(b) by 0 days.

(21) Appl. No.: 17/559,024

(22) Filed: Dec. 22, 2021

(65) Prior Publication Data

US 2022/0110279 A1 Apr. 14, 2022

Related U.S. Application Data

(60) Provisional application No. 63/182,184, filed on Apr. 30, 2021.

(51) Int. Cl.
*A01H 6/04* (2018.01)
*A01H 5/04* (2018.01)

(52) U.S. Cl.
CPC ............... *A01H 6/045* (2018.05); *A01H 5/04* (2013.01)

(58) Field of Classification Search
CPC .................................. A01H 5/04; A01H 5/06
USPC ......................................................... 800/298
See application file for complete search history.

(56) References Cited

U.S. PATENT DOCUMENTS

| 10,285,361 B2 * | 5/2019 | Watson .................... A01H 5/06 |
| 2015/0126380 A1 | 5/2015 | Van Dun |
| 2015/0245570 A1 | 9/2015 | Vogelaar et al. |

OTHER PUBLICATIONS

"Calibration Book-Onion and Shallot", Naktuinbouw Calibration Book, Allium cepa (Cepa Group), Allium cepa (Aggregatum Group) and Allium oschaninii O. Fedtsch. and hybrids between them—Onion, Echalion, Shallot, Grey Shallot, Version 1, Dec. 2010, 78 pages.
"Guidelines for the conduct of tests for Distinctness, Uniformity and Stability—Onion, Echalion; Shallot; Grey Shallot—UPOV Code(s): ALLIU_CEP_CEP, ALLIU_CEP_AGG, ALLIU_OSC (Allium cepa (Cepa Group), Allium cepa (Aggregatum Group) and Allium oschaninii O. Fedtsch. and hybrids between them)", UPOV, International Union for the Protection of New Varieties of Plants, Geneva, TG/46/7, Apr. 9, 2008, 42 pages.

"Objective description of Variety: Onion (*Allium cepa* L.)", US Department of Agriculture, Agricultural Marketing Service, Science and Technology, Plant Variety Protection Office, Exhibit C, Jun. 2015, 3 pages.
Arnhold-Schmitt, et al., "Physiological Aspects of Genome Variability in Tissue Culture. I. Growth Phase-Dependent Differential DNA Methylation of the Onion Genome (*Daucus carota* L.) During Primary Culture", Theoretical and Applied Genetics, vol. 91, Issue 5, Oct. 1995, pp. 809-815.
Jhang, et al., "Efficiency of different marker systems for molecular characterization of subtropical carrot germplasm", The Journal of Agricultural Science, vol. 148, Issue 2, Jan. 22, 2010, pp. 171-181.
Larkin, et al., "Somaclonal variation—a novel source of variability from cell cultures for plant improvement", Theoretical and Applied Genetics, vol. 60, Issue 4, 1981, pp. 197-214.
Martin, et al., "Identification of markers linked to agronomic traits in globe artichoke", Australian Journal of Crop Science, vol. 1, Issue 2, 2008, pp. 43-46.
Needleman, et al., "A general method applicable to the search for similarities in the amino acid sequence of two proteins". Journal of Molecular Biology, vol. 48, Issue 3, 1970, pp. 443-453.
Nikolova, et al., "Diploidization of cucumber (*Cucumis sativus* L.) haploids by colchicine treatment", Acta Societas Botanicorum Poloniae, vol. 65, Issue 3-4, 1996, pp. 311-317.
Nuñez, et al. "Carrot Production in California", University of California Agriculture and Natural Resources, Publication 7226, 2008, pp. 1-5.
Rice, et al., "EMBOSS: The European Molecular Biology Open Software Suite", Trends in Genetics, vol. 16, Issue 6, Jun. 1, 2000, pp. 276-277.
Robert W. Allard, "Overview of Plant Breeding", Principles of Plant Breeding, 2nd Edition, May 26, 1999, pp. 64-67.
Shim, et al., "Genetic structure in cultivated and wild carrots (*Daucus carota* L.) revealed by AFLP analysis", Theoretical and Applied Genetics, vol. 101, Issue 1, 2000, pp. 227-233.
Smith, et al., "Fresh-market bulb onion production in California", University of California Agriculture and Natural Resources, Publication 7242, 2011, pp. 1-6.
Songstad, et al., "Genome Editing of Plants", Critical Reviews in Plant Sciences, vol. 36, Issue 1, 2017, pp. 1-23.
Stein, et al., "Some remarks on carrot breeding (Daucus carota sativus Horffm.)", Plant Breeding, vol. 114, Issue 1, Feb. 1995, pp. 1-11.
Vos, et al., "AFLP: a new technique for DNA fingerprinting", Nucleic Acids Research, vol. 23, Issue 21, Nov. 11, 1995, pp. 4407-4414.
Wijnker, et al., "Hybrid recreation by reverse breeding in *Arabidopsis thaliana*", Nature Protocols, vol. 9, Issue 4, Mar. 6, 2014, pp. 761-772.

* cited by examiner

*Primary Examiner* — June Hwu
(74) *Attorney, Agent, or Firm* — ArentFox Schiff LLP

(57) ABSTRACT

A hybrid onion variety NUN 07212 ONL is disclosed as well as seeds and plants and bulbs thereof. Onion variety NUN 07212 ONL is a globe shape, long day onion variety.

26 Claims, 6 Drawing Sheets

ONION VARIETY NUN 07212 ONL

CROSS-REFERENCE TO RELATED APPLICATION

This application claims priority to U.S. Provisional Application No. 63/182,184 filed on Apr. 30, 2021, which is hereby incorporated by reference in its entirety.

FIELD OF THE DISCLOSURE

The present disclosure relates to the field of plant breeding and, more specifically, to onion variety NUN 07212 ONL. The disclosure further relates to vegetative reproductions of onion variety NUN 07212 ONL, methods for tissue culture of onion variety NUN 07212 ONL and regenerating a plant from such a tissue culture, and also to phenotypic variants of onion variety NUN 07212 ONL. The disclosure also relates to progeny of onion variety NUN 07212 ONL and the hybrid varieties obtained by crossing onion variety NUN 07212 ONL as a parent line with plants of other varieties or parent lines.

BACKGROUND OF THE DISCLOSURE

The goal of vegetable breeding is to combine various desirable traits in a single variety or hybrid. Such desirable traits may include greater yield, resistance to diseases, insects or other pests, tolerance to heat and drought, better agronomic quality, higher nutritional value, enhanced growth rate and improved bulb properties.

Breeding techniques take advantage of a plant's method of pollination. There are two general methods of pollination: a plant self-pollinates if pollen from one flower is transferred to the same or another flower of the same genotype. A plant cross-pollinates if pollen comes to it from a flower of a different genotype. Plants that have been self-pollinated and selected for (uniform) type over many generations become homozygous at almost all gene loci and produce a uniform population of true breeding progeny of homozygous plants. A cross between two such homozygous plants of different lines produces a uniform population of hybrid plants that are heterozygous for many gene loci. The extent of heterozygosity in the hybrid is a function of the genetic distance between the parents. Conversely, a cross of two plants each heterozygous at a number of loci produces a segregating population of hybrid plants that differ genetically and are not uniform. The resulting non-uniformity makes performance unpredictable.

The development of uniform varieties requires the development of homozygous inbred plants, the crossing of these inbred plants to make hybrids, optionally three-way hybrids, and the evaluation of the hybrids resulting from the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new plants are evaluated to determine which have commercial potential.

Onions belong to the lily family, Amaryllidaceae, and the genus *Allium*. Alliums comprise a group of perennial herbs having bulbous, onion-scented underground leaves, commonly known as onion bulbs, including such commonly cultivated crops as garlic, chives, and shallots. It also includes ornamental species grown for their flowers.

Onion is a cool-season, biannual crop and is one of the oldest cultivated vegetables in history. In 2017, worldwide production reached 93 million tons with China and United States ranking first and fourth. In general, the bulb is harvested and eaten. The common garden onions belong to the species *Allium cepa*.

Onions are generally classified by market use (green, fresh bulb, or dehydration bulb), bulb color (yellow, white, red), day-length requirement (short, intermediate, or long), flavor, or bulb shape (rounded or globed, flattened, or tapering cylindrical).

Onions that are commercially available in the market include 'fresh onions,' 'storage onions,' 'pearl or mini onions,' and 'green onions'. Fresh onions tend to have a lighter color with a thin skin, a milder, sweeter flavor, and must be eaten fresh as they do not store well. Storage onions have a darker skin that is thicker than that of a fresh onion. They are also known for intense, pungent flavor, higher percentage of solids, and desirable cooking characteristics. Storage onions are available from harvest, which is at the beginning of August, and are stored and available throughout the winter months up to about March. A true storage onion is one that can be harvested in late summer or fall, and stored, under proper conditions, until the spring, when the fresh onion crop is again available. Fresh and storage onions are available in red, yellow, and white colors. Pearl onions are mild, small, marble-sized onions, which are commonly used for pickling. Green onions or also referred to as spring onions or scallions are onions that have tubular green leaves and does not have fully developed bulbs, which can be eaten either raw or cooked.

Classification by day-length requirement are based on the degree of day length that will initiate bulb formation or bulbing. Bulbing is initiated when both the temperature and a minimum number of daylight hours reach certain levels resulting to leaf bases to swell to form storage tissue. When onions are first planted, they initially develop their vegetative growth, with no sign of bulb formation until the proper day length for that onion variety triggers the signal to the plant to stop producing above ground vegetative growth and start forming a bulb. Onions are thus sensitive to the hours of daylight and darkness they receive, and for most varieties it is only when the specific combination of daylight and darkness is reached, that the bulb starts to form. Onions are described as short-, intermediate-, and long-day length types. Short day means that bulbing will initiate at 11 to 12 hours of daylight. Intermediate day is used for onions bulbing at 12 to about 14 hours of daylight. Long day onions require about 14 or more hours of daylight for bulb formation to start.

Growers producing onions in more northerly climates plant long-day length onions. Daylight length varies greatly with latitude and at higher latitudes, long-day onions will produce sufficient top growth before the day length triggers bulbing to produce a large bulb. A short-day onion grown in the North (higher latitudes) will bulb too early and produce relatively small bulbs.

'Spanish onion,' 'Spanish onions,' or 'Spanish type' are terms applied to various long-day onions, generally yellow, though some white, and generally varieties that are large and globe-shaped. Spanish onion is commonly applied to various long day type onions of the type grown in western states of the United States (California, Idaho, Oregon, Washington, Colorado) with a bulb size averaging 300-700 grams (g) (typically over 3 inches up to 4 inches but also up to 5 inches in diameter for bulbs classified as "colossal").

Short day onions are preferred for southern areas such as southern Texas, southern California and Mexico. If a long day type onion is planted in such a short day climate, it may never experience enough day length to trigger the bulbing process.

Short day varieties do not keep well in storage conditions, and the pungency of short day varieties can climb considerably during storage. Present production in North America and Europe allows harvest of short day onions from mild winter regions from November through April. Long day onions are available fresh in the late summer and as storage onions from September through March, or even year round, have not been available in low pungency varieties (with the exception of U.S. patent application Ser. No. 12/861,740 (now U.S. Pat. No. 8,816,155), which is based on patent application Ser. No. 12/020,360, now abandoned). Sweet onions must be imported from the southern hemisphere to fill the gap in sweet onion production (November-February). In the United States, regions like Georgia and Texas produce short day onions from March to June, while low pungency onions available from November to February are short day onions, produced in the southern hemisphere.

Onions are also classified on flavor, with the common designations of sweet, mild, and pungent. The flavor of the onion is a result of both the type of onion and the growing conditions. For instance, soils containing a high amount of sulfur result in more pungent flavored onions. Sweetness in onions is caused by the sugar's glucose, fructose and sucrose. Onions also contain polymers of fructose called fructans. Onion cultivars differ quite markedly in the relative amounts of sucrose, glucose, fructose and fructans which they contain. They also differ in sugars according to length of storage and location in the bulb. Short day cultivars, which are poor storers, tend to have higher levels of sucrose, fructose and glucose, but hardly any of the fructans. In contrast, long day type cultivars and intermediate storage cultivars such as Pukekohe Longkeeper have less sucrose, glucose and fructose and higher amounts of fructans.

SUMMARY OF THE VARIOUS ASPECTS OF THE DISCLOSURE

The disclosure provides for onion variety NUN 07212 ONL, products thereof, and methods of using the same. NUN 07212 ONL is a globe shape, long day onion variety and is suitable for the open field.

The disclosure also provides for an onion plant or part thereof which has all of the morphological and physiological characteristics of onion variety NUN 07212 ONL when grown under the same environmental conditions.

In another aspect, the plant of variety NUN 07212 ONL or progeny thereof has 14, 15, or more or all of the following distinguishing characteristics when compared to the Reference Variety as shown in Table 3: 1) intermediate plant habit; 2) dark green leaf color; 3) erect foliage attitude; 4) darker intensity of foliage green color; 5) absent or weak foliage cranking; 6) shorter bulb height; 7) larger bulb diameter; 8) medium height/diameter ratio; 9) darker (golden) brown bulb skin color; 10) lighter white bulb interior color; 11) heavier bulb weight; 12) circular bulb shape in longitudinal section; 13) rounded shape of bulb stem end; 14) flat shape of bulb root end; and 15) thinner dry skin, when determined at 5% significance level for numerical characteristics and determined by type or degree for non-numerical characteristics for plants grown under the same environmental conditions.

In another aspect, the disclosure provides an onion plant or part thereof having all of the physiological and morphological characteristics of onion variety NUN 07212 ONL when grown under the same environmental conditions. The disclosure also provides for a progeny of onion variety NUN 07212 ONL. In a further aspect, the plant or progeny retains all or all but one, two, or three of the "distinguishing characteristics" of onion variety NUN 07212 ONL, or all but one, two, or three of the "physiological and morphological characteristics" of onion variety NUN 07212 ONL and methods of producing that plant or progeny.

In one aspect, the disclosure provides a plant or a progeny having all the physiological and morphological characteristics of onion variety NUN 07212 ONL when grown under the same environmental conditions. In another aspect, the plant or such progeny has all or all but one, two, or three of the physiological and morphological characteristics of onion variety NUN 07212 ONL when measured under the same environmental conditions and e.g., evaluated at significance levels of 1%, 5%, or 10% significance (which can also be expressed as p-value) for quantitative characteristics and identical (same type or degree) for non-quantitative characteristics, wherein a representative sample of seed of onion variety NUN 07212 ONL has been deposited under Accession Number NCIMB 43755. In another aspect, the plant or progeny has all or all but one, two, or three of the physiological and morphological characteristics as listed in Tables 1 and 2 of onion variety NUN 07212 ONL, when grown under the same environmental conditions and e.g., evaluated at significance levels of 1%, 5% or 10% significance (which can also be expressed as a p-value) for quantitative characteristics and identical (same type or degree) for non-quantitative characteristics.

In one aspect, the disclosure provides a seed of onion variety NUN 07212 ONL, wherein a representative sample of said seed has been deposited under Accession Number NCIMB 43755. The disclosure also provides for a plurality of seeds of onion variety NUN 07212 ONL. The onion seed of onion variety NUN 07212 ONL may be provided as an essentially homogeneous population of onion seed. The population of seed of onion variety NUN 07212 ONL may be particularly defined as being essentially free from other seed. The seed population may be grown into plants to provide an essentially homogeneous population of onion plants as described herein.

The disclosure also provides an onion plant grown from a seed of onion variety NUN 07212 ONL and a plant part thereof.

The disclosure also provides an onion bulb produced on a plant grown from a seed of onion variety NUN 07212 ONL.

In another aspect, the disclosure provides for a plant part obtained from onion variety NUN 07212 ONL, wherein said plant part is: a bulb, a harvested bulb, parts of bulbs, scales, part of scales, a bulblet, leaf, parts of a leaf, a part of a leaf, pollen, an ovule, a cell, a petiole, a shoot or a part thereof, a stem or a part thereof, a cutting, a seed, a part of a seed, seed coat or another maternal tissue which is part of a seed grown on said variety, a hypocotyl, a cotyledon, a pistil, an anther, and a flower or a part thereof. Bulbs are particularly important plant parts. In another aspect, the plant part obtained from onion variety NUN 07212 ONL is a cell, optionally a cell in a cell or tissue culture. That cell may be grown into a plant of onion variety NUN 07212 ONL.

In another aspect, the disclosure provides for a hybrid onion variety NUN 07212 ONL.

The disclosure also provides a cell culture of onion variety NUN 07212 ONL and a plant regenerated from onion variety NUN 07212 ONL, wherein the plant has all or all but one, two, or three of the morphological and physiological characteristics of onion variety NUN 07212 ONL, when grown under the same environmental conditions, as well as methods for culturing and regenerating onion variety NUN 07212 ONL. Alternatively, a regenerated plant may have one characteristic that is different from onion variety NUN 07212 ONL.

The disclosure further provides a vegetatively propagated plant of variety NUN 07212 ONL or part thereof, wherein the plant or part thereof has all or all but one, two, or three of the morphological and physiological characteristics of onion variety NUN 07212 ONL, when grown under the same environmental conditions as well as methods for vegetatively propagating onion variety NUN 07212 ONL.

In another aspect, the disclosure provides a method of producing an onion plant comprising crossing onion variety NUN 07212 ONL with another onion variety and selecting a progeny onion variety from said crossing.

The disclosure also provides a method of producing an onion plant derived from onion variety NUN 07212 ONL.

In a further aspect, the disclosure provides a method of producing hybrid onion seeds, comprising crossing a first parent onion plant with a second parent onion plant and harvesting the resultant hybrid onion seed, wherein said first parent onion plant or second parent onion plant is onion variety NUN 07212 ONL. Also provided is a hybrid onion seed produced from crossing a first parent onion plant with a second parent onion plant and harvesting the resultant seed, wherein first said first parent onion plant or second parent onion plant is onion variety NUN 07212 ONL. Moreover, the hybrid onion plant grown from the hybrid onion seed is provided.

In another aspect, the disclosure provides a method of introducing a single locus conversion into the plant of variety NUN 07212 ONL, wherein a representative sample of seed of seed of said onion variety has been deposited under Accession Number NCIMB 43755, wherein the plant otherwise has all of the morphological and physiological characteristics of onion variety NUN 07212 ONL and further comprises the single locus conversion.

In yet another aspect, the disclosure provides a method of introducing a desired trait into onion variety NUN 07212 ONL, said method comprises transforming the plant of variety NUN 07212 ONL with a transgene that confers the desired trait, wherein the transformed plant has otherwise all of the morphological and physiological characteristics of onion variety NUN 07212 ONL and contains the desired trait.

The disclosure also provides a method of producing a modified onion variety with a desired trait, wherein the method comprises mutating an onion plant or plant part of variety NUN 07212 ONL, wherein a representative sample of seed of said onion variety has been deposited under Accession Number NCIMB 43755, and wherein the mutated plant otherwise retains all of the morphological and physiological characteristics of onion variety NUN 07212 ONL and contains the desired trait.

In one aspect, the single locus conversion or desired trait is yield, size, shape, color, flavor, storage properties, nutritional quality, post-harvest quality, male sterility, herbicide tolerance, insect resistance, pest resistance, disease resistance, environmental stress tolerance, modified carbohydrate metabolism, or modified protein metabolism.

In another aspect, the disclosure provides a container comprising the plant, plant part, or seed of onion variety NUN 07212 ONL.

Also provided is a food, a feed, or a processed product comprising the plant part of onion variety NUN 07212 ONL, wherein the plant part is a bulb or part thereof.

DEFINITIONS

Figure 1:
FIG. 1 shows the plant of onion variety NUN 07212 ONL.
Figure 2:
FIG. 2 shows the plant attitude comparison of onion variety NUN 07212 ONL and the Reference Variety.
Figure 3:
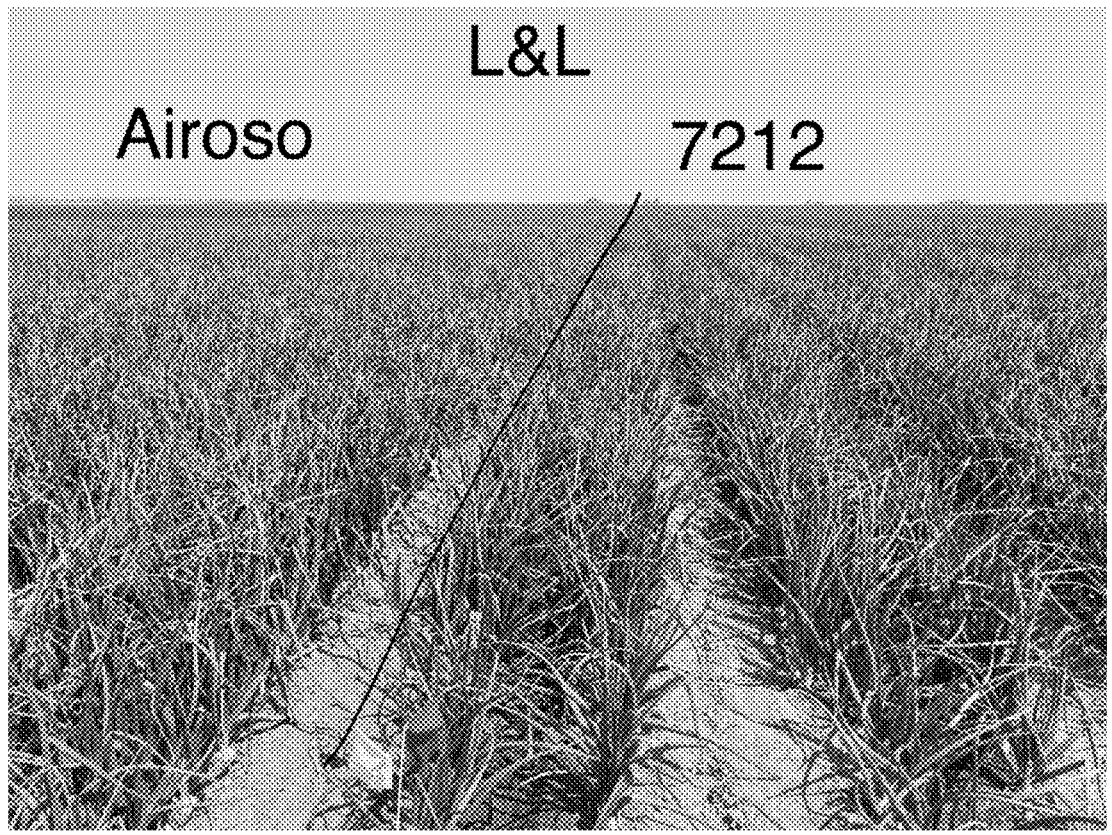
FIG. 3 shows the plant comparison of onion variety NUN 07212 ONL and the Reference Variety.
Figure 4:
FIG. 4 shows the bulbs of onion variety NUN 07212 ONL.
Figure 5:
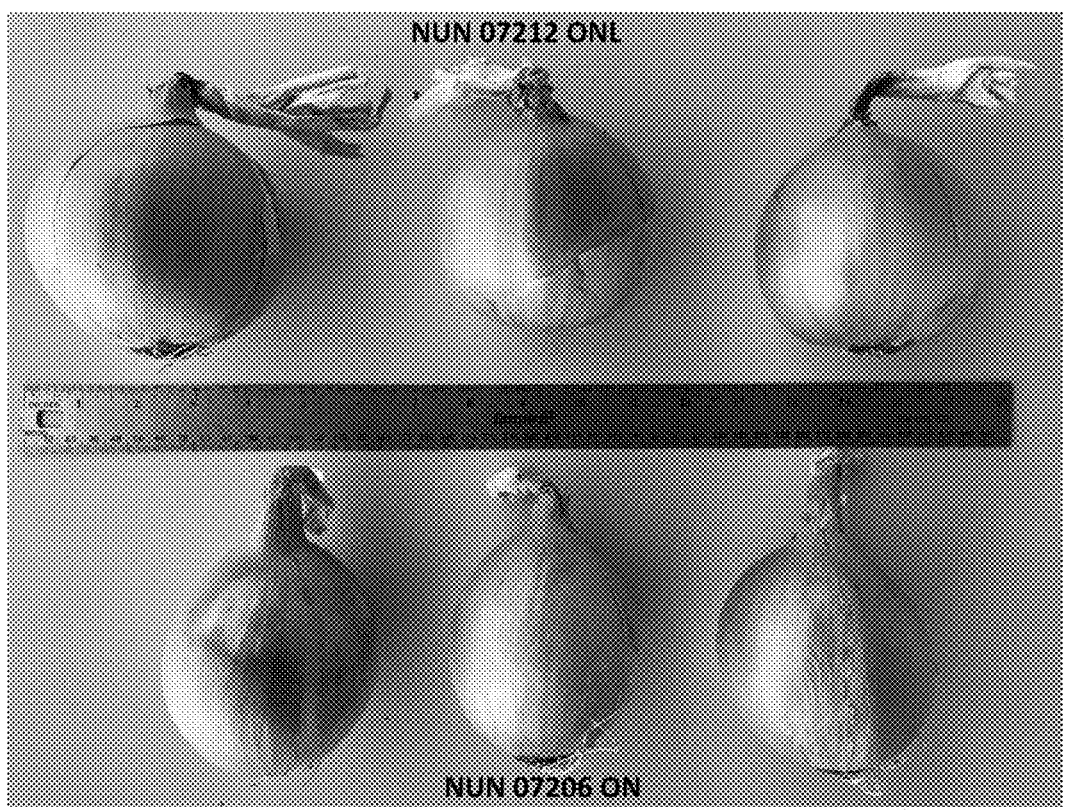
FIG. 5 shows the bulb comparison of onion variety NUN 07212 ONL and the Reference Variety.
Figure 6:
FIG. 6 shows the cross-section comparison of onion variety NUN 07212 ONL and the Reference Variety.
Figure 7:
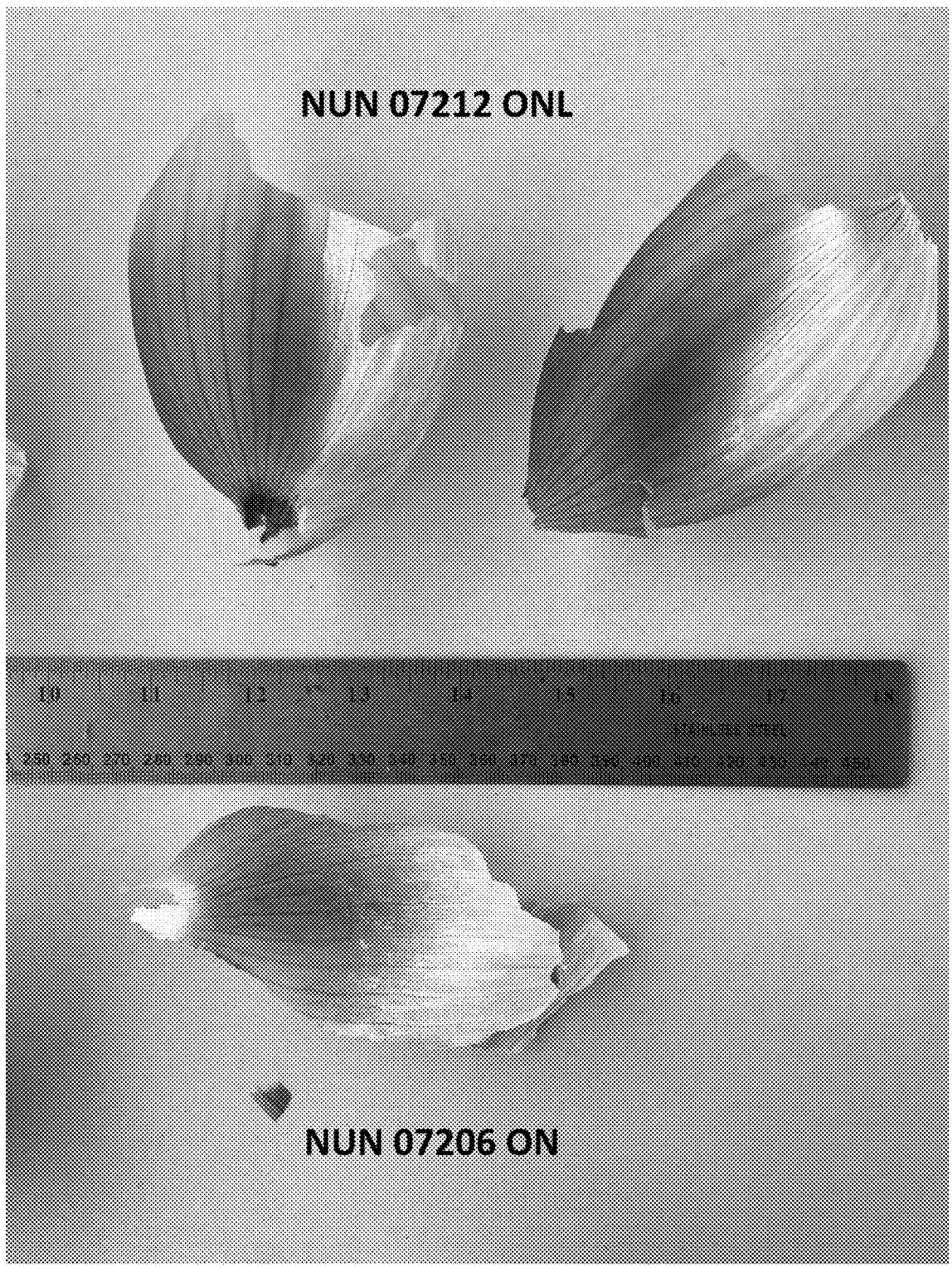
FIG. 7 shows the skin thickness comparison of onion variety NUN 07212 ONL and the Reference Variety.

Onion plant" or "onion" is a plant of genus *Allium* or a part thereof (e.g. a bulb). Onion includes, e.g., *Allium aggregatum* (e.g., chalottes and potato onion), *Allium cepa* and *Allium fistulosum*, as well as crossbreds thereof, and hybrids such as *Allium* x *proliferum, Allium* x *wakegi*, and the triploid onion *Allium* x *cornutum*.

"Biennial plant" means that *Allium cepa* L. produces a bulb in the first season and seeds in the second.

"Cultivated onion" refers to plants of *Allium* (e.g., varieties, breeding lines or cultivars of the species *Allium cepa* as well as crossbreds with *Allium aggregatum* and *Allium fistulosum*), cultivated by humans and having good agronomic characteristics.

The terms "onion plant designated NUN 07212 ONL", "NUN 07212 ONL", "NUN 07212", "NUN 07212 F1" "07212 ONL," "onion 07212," or "Glorioso" are used interchangeably herein and refer to an onion plant of variety NUN 07212 ONL, representative sample of seed of said onion variety has been deposited under Accession Number NCIMB 43755.

"Plant" includes the whole plant or any parts or derivatives thereof, having the same genetic makeup as the plant from which it is obtained.

"Plant part" includes any part of a plant, such as a plant organ (e.g., harvested or non-harvested onion bulbs), a plant cell, a plant protoplast, a plant cell tissue culture or a tissue culture from which a whole plant can be regenerated, a plant cell that is intact in a plant, a clone, a micropropagation, a plant callus, a plant cell clump, a plant transplant, a vegetative propagation, a seedling, or a part of a plant (e.g., harvested tissues or organs), such as a bulb, or a part of a bulb, a harvested bulb, a root, or a part of a root, a harvested root, a root tip, a fruit, a harvested fruit, a part of a fruit, a leaf, a part of a leaf, pollen, an ovule, an embryo, a petiole, a shoot or a part thereof, a stem or a part thereof, a cutting, a seed, a part of a seed, seed coat or another maternal tissue, hypocotyl, cotyledon, a pistil, an anther, and a flower or parts of any of these and the like. Seed can be mature or immature. Pollen or ovules may be viable or non-viable. Also, any developmental stage is included, such as seedlings, cuttings prior or after rooting, mature plants or leaves. Alternatively, a plant part may also include a plant seed which comprises maternal tissues of onion variety NUN 07212 ONL, and an embryo having one or two sets of chromosomes derived from the parent plant, e.g., from onion variety NUN 07212 ONL. Such an embryo comprises two sets of chromosomes derived from onion variety NUN 07212 ONL, if it produced from self-pollination of said variety, while an embryo derived from cross-fertilization of onion variety NUN 07212 ONL will comprise only one set of chromosomes from onion variety NUN 07212 ONL and the other set of chromosomes from the other parent.

A "seed of NUN 07212 ONL" refers to an onion seed which can be grown into a plant of onion variety NUN 07212 ONL, wherein a representative sample of viable seed of onion variety NUN 07212 ONL has been deposited under Accession Number NCIMB 43755. A seed can be in any stage of maturity, for example, a mature, viable seed, or an immature, non-viable seed. A seed comprises an embryo and maternal tissues.

An "embryo of NUN 07212 ONL" refers to an "F1 hybrid embryo" as present in a seed of onion variety NUN 07212 ONL, a representative sample of said seed of onion variety NUN 07212 ONL has been deposited under Accession Number NCIMB 43755.

A "seed grown on NUN 07212 ONL" refers to a seed grown on a mature plant of onion variety NUN 07212 ONL. The "seed grown on NUN 07212 ONL" contains tissues and DNA of the maternal parent, onion variety NUN 07212 ONL.

An "essentially homogeneous population of onion seed" is a population of seeds where at least 97%, 98%, or 99% or more of the total population of seed are seeds of onion variety NUN 07212 ONL.

An "essentially homogeneous population of onion plants" is a population of plants where at least 97%, 98%, 99% or more of the total population of plants are plants of onion variety NUN 07212 ONL.

The phrase "essentially free from other seed" refers to a population of seed where less than 3%, 2%, 1% or less of the total population of seed is seed that is not an onion seed or, in another aspect, less than 3%, 2%, 1% or less of the total population of seed is seed that is not a seed of onion variety NUN 07212 ONL.

"Bulb" or "onion bulb" refers to the commercially/harvested or harvestable edible portion of the onion plant. An onion bulb comprises an apex and concentric, enlarged fleshy leaf bases, also called fleshy scale leaves. Onion bulbs may be developing onion bulbs or mature onion bulbs. A small bulb or a bulb early in its development or a secondary bulb developing on the main bulb may described as a bulblet.

"Harvested plant material" refers herein to plant parts which have been collected for further storage and/or further use.

"Harvested seeds" refers to seeds harvested from a line or variety, e.g. produced after self-fertilization or cross-fertilization and collected.

"Maturity" refers to the development stage of an onion bulb when said onion bulb has fully developed (reached its final size). In particular, "maturity" is defined as the mature state of bulb development and optimal time for harvest. Typically, maturity of a bulb is reached when the vegetative phase of an onion plant is over, and leaves and neck of the onion plant dry out.

"Harvest maturity" is referred to as the stage at which an onion bulb is ready for harvest or the optimal time to harvest the bulb. In one embodiment, harvest maturity is the stage where 25-50% of the onion leaf tops have fallen over.

A "mature onion bulb" refers to any onion bulb that is ready for harvest. Generally, when 25-50% of the onion leaf tops have fallen over, the onion is ready for harvest.

"Yield" means the total weight of all onion bulbs harvested per hectare of a particular line or variety. It is understood that "yield" expressed as weight of all onions harvested per hectare can be obtained by multiplying the number of plants per hectare times the "yield per plant".

"Marketable yield" means the total weight of marketable onion bulbs harvested per hectare of a particular line or variety, i.e., bulbs suitable for being sold for fresh consumption, having acceptable shape, moisture, pungency, and no or very low levels of deficiencies.

"USDA descriptors" are the plant variety descriptors described for onion in the "Objective description of Variety—Onion (*Allium cepa* L.)," as published by U.S. Department of Agriculture, Agricultural Marketing Service, Science and Technology, Plant Variety Protection Office, Beltsville, Md. 20705 and which can be downloaded from the world-wide web at ams.usda.gov/ under services/plant-variety-protection/pvpo-c-forms under onion. "Non-USDA descriptors" are other descriptors suitable for describing onion.

"UPOV descriptors" are the plant variety descriptors described for onion in the "Guidelines for the Conduct of Tests for Distinctness, Uniformity and Stability, TG/46/7 (Geneva, 2008), as published by UPOV (International Union for the Protection of New Varieties and Plants) and which can be downloaded from the world wide web at upov.int/ under edocs/tgdocs/en/tg049.pdf and is herein incorporated by reference in its entirety. Likewise, "UPOV methods" to determine specific parameters for the characterization of onion are described at upov.int.

"Calibration book Onion and Shallot" refers to the calibration book for onion which provides guidance for describing an onion variety, as published by Naktuinbow (Netherlands), December 2010 and based on the UPOV Guideline TG/13.

"RHS" or "RHS color" refers to the Royal Horticultural Society (UK), which publishes an official botanical color chart quantitatively identifying colors according to a defined numbering system. The chart may be purchased from Royal Horticulture Society Enterprise Ltd RHS Garden; Wisley, Woking; Surrey GU236QB, UK, e.g., the RHS color chart: 2007.

"Reference Variety" for onion NUN 07212 ONL refers herein to variety NUN 07206 ONL, a commercial variety from Nunhems B.V. with commercial name Airoso. In Tables 1 and 2, a comparison between onion variety NUN 07212 ONL and the Reference Variety is shown. The distinguishing characteristics between onion variety NUN 07212 ONL and the Reference Variety are shown in Table 3.

A plant having "all the physiological and morphological characteristics" of a referred-to-plant means a plant showing the physiological and morphological characteristics of the referred-to-plant when grown under the same environmental conditions, preferably in the same experiment; the referred-to-plant can be a plant from which it was derived, e.g., the progenitor plant, the parent, the recurrent parent, the plant used for tissue- or cell culture, etc. A physiological or morphological characteristic can be a numerical characteristic or a non-numerical characteristic. In one aspect, a plant has "all but one, two, or three of the physiological and morphological characteristics" of a referred-to-plant, or "all the physiological and morphological characteristics" of Tables 1 and 2 or "all or all but one, two, or three of the physiological and morphological characteristics" of Tables 1 and 2.

The physiological and/or morphological characteristics mentioned above are commonly evaluated at significance levels of 1%, 5%, or 10% if they are numerical (quantitative), or for having an identical degree (or type) if not numerical, if measured under the same environmental conditions. For example, a progeny plant or a Single Locus Converted plant or a mutated plant of onion variety NUN 07212 ONL may have one or more (or all) of the essential physiological and/or morphological characteristics of said variety listed in Tables 1 and 2, as determined at the 5% significance level (i.e., p<0.05), when grown under the same environmental conditions.

"Distinguishing characteristics" or "distinguishing morphological and/or physiological characteristics" refers herein to the characteristics which distinguish the new variety from the other onion varieties, such as the Reference Variety (i.e., are different), when grown under the same environmental conditions. The distinguishing characteristics between onion variety NUN 07212 ONL and the Reference Variety are described herein and are presented in Table 3. When comparing onion variety NUN 07212 ONL to other varieties, the distinguishing characteristics may be different. In one aspect, the distinguishing characteristics may therefore include at least one, two, three or more (or all) of the characteristics listed in Tables 1 and 2. All numerical distinguishing characteristics are statistically significantly different at p<0.05 between onion variety NUN 07212 ONL and the other variety (e.g., Reference Variety).

Onion variety NUN 07212 ONL has the following distinguishing characteristics when compared to the Reference Variety as shown in Table 3: 1) intermediate plant habit; 2) dark green leaf color; 3) erect foliage attitude; 4) darker intensity of foliage green color; 5) absent or weak foliage cranking; 6) shorter bulb height; 7) larger bulb diameter; 8) medium height/diameter ratio; 9) darker (golden) brown bulb skin color; 10) lighter white bulb interior color; 11) heavier bulb weight; 12) circular bulb shape in longitudinal section; 13) rounded shape of bulb stem end; 14) flat shape of bulb root end; and 15) thinner dry skin, when determined at 5% significance level for numerical characteristics and determined by type or degree for non-numerical characteristics for plants grown under the same environmental conditions.

Thus, an onion plant "comprising the distinguishing characteristics of variety NUN 07212 ONL" (such as a progeny plant) refers herein to a plant which does not differ significantly from said variety in the distinguishing characteristics above. Therefore, in one aspect a plant is provided which does not differ significantly from onion variety NUN 07212 ONL in the distinguishing characteristics above.

Similarity and differences between two different plant lines or varieties can be determined by comparing the number of morphological and/or physiological characteristics that are the same (i.e., statistically not significantly different) or that are different (i.e., statistically significantly different) between the two plant lines or varieties grown under the same environmental conditions. A numerical characteristic is considered to be "the same" when the value for a numeric characteristic is not significantly different at the 1% (p<0.01) or 5% (p<0.05) significance level, using the T-Test, a standard method known to the skilled person. A non-numerical characteristic is considered to be "the same" when the values have the same "degree" or "type" when scored using USDA and/or UPOV descriptors, for plants are grown under the same environmental conditions.

In one aspect, a statistical analysis of quantitative characteristics showing the degree of significance may be provided. Statistical significance is the likelihood that a relationship between two or more variables is caused by something other than chance, i.e., that the differences in the means for quantitative characteristics of onion variety NUN 07212 ONL and the Reference Variety are significant or due to chance. For the purpose of proving differences or distinction between onion variety NUN 07212 ONL and the Reference Variety, a p-value of 5% (or 0.05) or lower is considered statistically significant. This means that there is only a 5% probability that the observed result could have happened just by chance or random variation.

The statistical analysis is drawn from a small sample of at least 15 plants or plants parts of onion variety NUN 07212 ONL and the Reference Variety. Statistical points or parameters such as mean, minimum, median, maximum, and standard deviation are collected from the sample data to analyze where the average is, how varied the data set is, and whether the data is skewed. For the purpose of determining whether the result of a data set is statistically significant, a T-test is used, a statistical tool for proving significance in the means of the two groups (e.g., onion variety NUN 07212 ONL and the Reference Variety) at 5% significance level (p-value of 5% or 0.05).

The term "traditional breeding techniques" encompasses herein crossing, selfing, selection, doubled haploid production, embryo rescue, protoplast fusion, marker assisted selection, mutation breeding etc. as known to the breeder (i.e., methods other than genetic modification/transformation/transgenic methods), by which, for example, a genetically heritable trait can be transferred from one onion line or variety to another.

"Variety," "cultivated onion," or "cultivar" means a plant grouping within a single botanical taxon of the lowest known rank.

A "plant line" is for example, a breeding line which can be used to develop one or more varieties. A breeding line is typically highly homozygous.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Progeny" as used herein refers to a plant obtained from a plant designated NUN 07212 ONL. A progeny may be obtained by regeneration of cell culture or tissue culture or parts of a plant of said variety or selfing of a plant of said variety or by producing seeds of a plant of said variety. In further aspects, progeny may also encompass plants obtained from crossing of at least one plant of said variety with another onion plant of the same variety or another variety or (breeding) line, or with wild onion plants. A progeny may comprise a mutation or a transgene. A "first generation progeny" or is the progeny directly derived from, obtained from, obtainable from or derivable from the parent plant by, e.g., traditional breeding methods (selfing and/or cross-pollinating) or regeneration (optionally combined with transformation or mutation). Thus, a plant of onion variety NUN 07212 ONL is the male parent, the female parent or both of a first generation progeny of onion variety NUN 07212 ONL. Progeny may have all the physiological and morphological characteristics of variety NUN 07212 ONL when grown under the same environmental conditions. Using common breeding methods such as backcrossing or recurrent selection, mutation or transformation, one or more specific characteristics may be introduced into said variety, to provide a plant comprising all but 1, 2, or 3 or more of the morphological and physiological characteristics of onion variety NUN 07212 ONL.

"Tissue culture" or "cell culture" refers to a composition comprising isolated cells of the same or a different type or a collection of such cells organized into parts of a plant. Tissue culture of various tissues of onion and regeneration of plants therefrom is well known and widely published (see, e.g., Arnholdt-Schmitt et al., 1995 Theor Appl Genet (1995) 91:809-815; Larkin and Scowcroft, (1981) Theor. Appl. Genet. 60, 197-214). Similarly, the methods of preparing cell cultures are known in the art.

"Vegetative propagation," "vegetative reproduction," or "clonal propagation" are used interchangeably herein and mean a method of taking a part of a plant and allowing that plant part to form at least roots, and also refer to the plant or plantlet obtained by that method. Optionally, the vegetative propagation is grown into a mature plant. The skilled person is aware of what plant parts are suitable for use in the method.

"Regeneration" refers to the development of a plant from cell culture or tissue culture or vegetative propagation.

"Crossing" refers to the mating of two parent plants. The term encompasses "cross-pollination" and "selfing".

"Selfing" refers to self-pollination of a plant, i.e., the transfer of pollen from the anther to the stigma of the same plant.

"Cross-pollination" refers to the fertilization by the union of two gametes from different plants.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce a progeny plant. Progeny plants which have the trait are then crossed to the recurrent parent. After several generations of backcrossing and/or selfing the recurrent parent comprises the trait of the donor. The plant generated in this way may be referred to as a "single trait converted plant". The technique can also be used on a parental line of a hybrid.

The terms "gene converted" or "conversion plant" or "single locus converted plant" in this context refer to onion plants which are developed by traditional breeding techniques, e.g., backcrossing or via genetic engineering or through mutation breeding, wherein essentially all of the desired morphological and physiological characteristics of the parent variety or line are recovered, in addition to the one or more characteristics introduced into the parent transferred into the parent via e.g., the backcrossing technique (optionally including reverse breeding or reverse synthesis of breeding lines). It is understood that only the addition of a further characteristics (e.g., addition of gene conferring a further characteristic, such as a disease resistance gene), but also the replacement/modification of an existing characteristics by a different characteristic is encompassed herein (e.g., mutant allele of a gene can modify the phenotype of a characteristic).

Likewise, a "Single Locus Converted (Conversion) Plant" refers to plants developed by plant breeding techniques comprising or consisting of mutation and/or by genetic transformation and/or by traditional breeding techniques, such as backcrossing, wherein essentially all of the desired morphological and physiological characteristics of an onion variety are recovered in addition to the characteristics of the single locus having been transferred into the variety via the backcrossing technique, or wherein the morphological and physiological characteristic of the variety has been replaced/modified in the variety. In case of a hybrid, the gene may be introduced in the male or female parental line.

"Transgene" refers to a genetic locus comprising a DNA sequence which has been introduced into the genome of an onion plant by transformation. A plant comprising a transgene stably integrated into its genome is referred to as "transgenic plant."

"Locus" (plural loci) refers to the specific location of a gene or DNA sequence on a chromosome. A locus may confer a specific trait.

"Genotype" refers to the genetic composition of a cell or organism.

"Allele" refers to one or more alternative forms of a gene locus. All of these loci relate to one trait. Sometimes, different alleles can result in different observable phenotypic traits. However, many variations at the genetic level result in little or no observable variation.

As used herein, the terms "resistance" and "tolerance" are used interchangeably to describe plants that show no symptoms or significantly reduced symptoms to a specified biotic pest, pathogen, abiotic influence or environmental condition compared to a susceptible plant. These terms are optionally also used to describe plants showing some symptoms but that are still able to produce marketable product with an acceptable yield.

DETAILED DESCRIPTION OF VARIOUS ASPECTS OF THE DISCLOSURE

The disclosure relates to the plant of onion variety NUN 07212 ONL, wherein a representative sample of seeds of said onion variety has been deposited under the Budapest Treaty, with Accession number NCIMB 43755. NUN 07212 ONL is a globe shape, long day onion variety and is suitable for the open field.

The disclosure also provides for an onion plant or part thereof having all of the physiological and morphological characteristics of onion variety NUN 07212 ONL when grown under the same environmental conditions.

The disclosure further relates to an onion variety NUN 07212 ONL, which when compared to its Reference Variety has the following distinguishing characteristics as shown in Table 3: 1) intermediate plant habit; 2) dark green leaf color; 3) erect foliage attitude; 4) darker intensity of foliage green color; 5) absent or weak foliage cranking; 6) shorter bulb height; 7) larger bulb diameter; 8) medium height/diameter ratio; 9) darker (golden) brown bulb skin color; 10) lighter white bulb interior color; 11) heavier bulb weight; 12) circular bulb shape in longitudinal section; 13) rounded shape of bulb stem end; 14) flat shape of bulb root end; and 15) thinner dry skin, when determined at 5% significance level for numerical characteristics and determined by type or degree for non-numerical characteristics for plants grown under the same environmental conditions. Also encompassed are parts of that plant.

In one aspect, the plant of onion variety NUN 07212 ONL or a progeny plant thereof, comprises all of the following morphological and/or physiological characteristics (i.e., average values of distinguishing characteristics, as indicated on the USDA Objective description of variety—onion (unless indicated otherwise)) as shown in Tables 1 and 2, where the numerical characteristics are determined at the 5% significance level and determined by type or degree for non-numerical characteristics for plants grown under the same environmental conditions. A part of this plant is provided.

The disclosure further provides an onion plant which does not differ from the physiological and morphological characteristics of the plant of onion variety NUN 07212 ONL as determined at the 1%, 2%, 3%, 4% or 5% significance level for numerical characteristics and determined by type or degree for non-numerical characteristics when grown under the same environmental conditions. In a particular aspect, the plants are measured in the same trial (e.g., the trial is conducted as recommended by the USDA or UPOV). The disclosure also comprises a part of said plant, preferably a bulb or a part thereof.

The morphological and/or physiological differences between two different individual plants described herein (e.g., between onion variety NUN 07212 ONL and a progeny of said onion variety) or between a plant of onion variety NUN 07212 ONL or progeny of said variety, or a plant having all, or all but 1, 2, or 3 of the physiological and morphological characteristics of onion variety NUN 07212 ONL and another known variety can easily be established by growing said variety next to each other or next to the other variety (in the same field, under the same environmental conditions (in the same field, optionally, next to each other), preferably in repeated several locations which are suitable for cultivation of onions, and measuring morphological and/or physiological characteristics of a representative number of plants (e.g., to calculate an average value and to determine the variation range/uniformity within the variety). For example, trials can be carried out in Acampo Calif., USA (N 38 degrees 07'261"/W 121 degrees 18' 807", USA), whereby various characteristics, for example, market maturity, plant habit, leaf color, leaf length, leaf width, sheath length, sheath diameter, sheath scape, inflorescence, bulb size, bulb shape, bulb height, bulb diameter, bulb skin color, scales, pungence, storage, disease resistance, insect resistance, can be measured and directly compared for species of onion.

Thus, the disclosure comprises onion plant having one, two, or three physiological and/or morphological characteristics which are different from those of the plant of onion variety NUN 07212 ONL and which otherwise has all the physiological and morphological characteristics of the plant of onion variety NUN 07212 ONL (e.g., at 5% significance level for numerical characteristic and determined by type or degree non-numerical characteristics) for plants grown under the same environmental conditions. In another aspect, the different characteristic is the result of a mutation (e.g., spontaneous mutation or human induced mutation through e.g., targeted mutagenesis or traditional mutagenesis such as chemically or radiation induced mutagenesis) or it is the result of a transformation.

The disclosure relates to a seed of onion variety NUN 07212 ONL, wherein a representative sample of said seed has been deposited under the Budapest Treaty, with Accession number NCIMB 43755.

In another aspect, a seed of hybrid onion variety NUN 07212 ONL is obtainable by crossing the male parent of onion variety NUN 07212 ONL with the female parent of onion variety NUN 07212 ONL and harvesting the seeds produced on the female parent. The resultant seeds of said variety can be grown to produce plants of said variety.

In another aspect, the disclosure provides an onion plant grown from a seed of onion variety NUN 07212 ONL and a plant part thereof.

In another aspect, the disclosure provides for an onion plant part of variety NUN 07212 ONL, preferably a bulb or part thereof, a representative sample of seed from said variety has been deposited under the Budapest Treaty, with Accession number NCIMB 43755.

Also provided is a plant of onion variety NUN 07212 ONL, or a bulb or other plant part thereof, produced from a seed, wherein a representative sample of said seeds has been deposited under the Budapest Treaty, with Accession Number NCIMB 43755.

Also provided is a plant part obtained from onion variety NUN 07212 ONL, wherein said plant part is: a bulb, or a part of a bulb, a harvested bulb, a bulblet, a leaf, a part of a leaf, pollen, an ovule, a cell, a petiole, a shoot or a part thereof, a stem or a part thereof, a cutting, a seed, a part of a seed, seed coat or another maternal tissue which is part of a seed grown on said variety, a hypocotyl, a cotyledon, a pistil, an anther, and a flower or a part thereof. Such plant parts may be suitable for sexual reproduction (e.g., a pollen, a flower or a part thereof), vegetative reproduction (e.g., a cutting, a bulb, a root, a stem, a cell, a protoplast, a leaf, a cotyledon, a meristem, etc.), or tissue culture (e.g., a leaf, a pollen, an embryo, a cotyledon, a hypocotyl, a cell, a root, a root tip, an anther, a flower, a seed, a stem, etc.). Bulbs are particularly important plant parts.

In a further aspect, the plant part obtained from onion variety NUN 07212 ONL is a cell, optionally a cell in a cell or tissue culture. That cell may be grown into a plant of onion variety NUN 07212 ONL. A part of onion variety NUN 07212 ONL (or of progeny of that variety or of a plant having all physiological and/or morphological characteristics but one, two, or three which are different from those of onion variety NUN 07212 ONL) further encompasses any cells, tissues, organs obtainable from the seedlings or plants in any stage of maturity.

The disclosure also provides a tissue or cell culture comprising cells of onion variety NUN 07212 ONL. Such a tissue culture can, for example, be grown on plates or in liquid culture, or be frozen for long term storage. The cells of onion variety NUN 07212 ONL used to start the culture can be selected from any plant part suitable for vegetative reproduction, or in a particular aspect can be selected from an embryo, a meristem, a cotyledon, a hypocotyl, pollen, a leaf, an anther, a bulb, a root, a root tip, a pistil, a petiole, a flower, a fruit, a seed, a stem and a stalk. In another particular aspect, the tissue culture does not contain somaclonal variation or has reduced somaclonal variation. The skilled person is familiar with methods to reduce or prevent somaclonal variation, including regular reinitiation.

In one aspect, the disclosure provides an onion plant regenerated from the tissue or cell culture of onion variety NUN 07212 ONL, wherein the regenerated plant is not significantly different from onion variety NUN 07212 ONL in all, or all but one, two, or three, of the physiological and morphological characteristics (e.g., determined at the 5% significance level for numerical characteristics and determined by degree/type for non-numerical characteristics) when grown under the same environmental conditions. Optionally, the plant has one, two, or three the physiological and morphological characteristics that are affected by a mutation or transformation with a transgene.

In another aspect, the disclosure provides an onion plant regenerated from the tissue or cell culture of onion variety NUN 07212 ONL, wherein the plant has all of the physiological and morphological characteristics of said variety determined (e.g., determined at the 5% significance level for numerical characteristics and determined by degree/type for non-numerical characteristics) when grown under the same environmental conditions. Similarity or difference of a characteristic is determined by measuring the characteristics of a representative number of plants grown under the same environmental conditions, determining whether type/degree characteristics are the same or different and determining whether numerical characteristics are different at the 5% significance level.

Onion variety NUN 07212 ONL, or its progeny, or a plant having all physiological and/or morphological characteristics but one, two, or three which are different from those of onion variety NUN 07212 ONL, can also be reproduced using vegetative reproduction methods. Therefore, the disclosure provides for a method of producing a plant, or a plant part of onion variety NUN 07212 ONL, comprising vegetative propagation of said variety. Vegetative propagation comprises regenerating a whole plant from a plant part of onion variety NUN 07212 ONL or from a progeny or from or a plant having all physiological and/or morphological characteristics of said variety but one, two, or three different characteristics, such as a cutting, a cell culture, or a tissue culture.

The disclosure also provides methods of vegetatively propagating a part of the plant of onion variety NUN 07212 ONL. In certain aspects, the method comprises: (a) collecting tissue or cells capable of being propagated from onion variety NUN 07212 ONL to obtain proliferated shoots; (b) rooting said proliferated shoots to obtain rooted plantlets. Steps (a) and (b) may also be reversed, i.e., first cultivating said tissue to obtain roots and then cultivating the tissue to obtain shoots, thereby obtaining rooted plantlets. The rooted plantlets may then be further grown, to obtain plants. In one aspect, the method further comprises step (c) growing plants from said rooted plantlets. Therefore, the method also comprises regenerating a whole plant from said part of onion variety NUN 07212 ONL. In a particular aspect, the part of the plant to be propagated is a cutting, a cell culture, or a tissue culture.

The disclosure also provides for a vegetatively propagated plant of onion variety NUN 07212 ONL (or from progeny of said variety or from or a plant having all but one, two, or three physiological and/or morphological characteristics of onion variety NUN 07212 ONL) wherein the plant has all of the morphological and physiological characteristics of onion variety NUN 07212 ONL (e.g., determined at the 5% significance level for numerical characteristics and determined by type/degree for non-numerical characteristics) for plants grown under the same conditions. In another aspect, the propagated plant has all but one, two, or three of the morphological and physiological characteristics of onion variety NUN 07212 ONL (e.g., determined at the 5% significance level for numerical characteristics and determined by type/degree for non-numerical characteristics) for plants grown under the same conditions. A part of said propagated plant or said propagated plant with one, two, or three differences is also provided. In another aspect, the propagated plant has all or all but one, two, or three of the morphological and physiological characteristics of onion variety NUN 07212 ONL (e.g., as listed in Tables 1 and 2).

In another aspect, the disclosure provides a method for producing an onion plant part, preferably a bulb or part thereof, comprising growing the plant of onion variety NUN 07212 ONL until it develops a bulb, and collecting the bulb. Preferably, the bulb is collected at harvest maturity. A plant of onion variety NUN 07212 ONL can be produced by seeding directly in the soil (e.g., field) or by germinating the seeds in controlled environment conditions, e.g., greenhouses and then transplanting the seedlings into the field. For example, the seed can be sown into prepared seed beds where they will remain for the entire production of the crop (see, e.g., Voss, et. al., University of California Agriculture and Natural Resources Communication Services, ISBN 978-1-60107-033.3, pp. 1-4).

In still another aspect, the disclosure provides a method of producing an onion plant, comprising crossing a plant of onion variety NUN 07212 ONL with a second onion plant at least once, allowing seed to develop and optionally harvesting said respective progeny seed. The skilled person can select progeny from said crossings. Optionally, the respective progeny is crossed twice, thrice, or four, five, six, or seven times, and allowed to set seed. In another aspect, the first step in "crossing" comprises planting seeds of a first and a second parent onion plant, often in proximity so that pollination will occur, for example, mediated by insect vectors. Alternatively, pollen can be transferred manually. Where the plant is self-pollinated, pollination may occur without the need for direct human intervention other than plant cultivation. After pollination the plant can produce seed.

The disclosure also provides a method for collecting pollen of onion variety NUN 07212 ONL, comprising collecting the pollen from a plant of onion variety NUN 07212 ONL. Alternatively, the method comprises growing a plant of onion variety NUN 07212 ONL until at least one flower contains pollen and collecting the pollen. In a particular aspect, the pollen is collected when it is mature or ripe. A suitable method for collecting pollen comprises collecting anthers or the part of the anther that contains pollen, for example, by cutting it off. Pollen can be collected in containers. Optionally, collected pollen can be used to pollinate an onion flower.

In yet another aspect, the disclosure provides a method of producing a plant, comprising selfing a plant of onion variety NUN 07212 ONL one or more times, and selecting a progeny plant from said selfing. In one aspect, the progeny plant retains all or all but one, two, or three of the morphological and physiological characteristics of onion variety NUN 07212 ONL, when grown under the same environmental conditions. In a different aspect, the progeny plant, comprises all (or all but one, two or three) of the physiological and morphological characteristic of onion variety NUN 07212 ONL as listed in Tables 1 and 2.

The disclosure also provides a method for developing an onion plant in an onion breeding program, using an onion plant of variety NUN 07212 ONL, or its parts as a source of plant breeding material. Suitable plant breeding techniques are recurrent selection, backcrossing, pedigree breeding, mass selection, mutation breeding and/or genetic marker enhanced selection. In one aspect, the method comprises crossing onion variety NUN 07212 ONL or progeny of said variety, or a plant comprising all but 1, 2, or 3 or more of the morphological and physiological characteristics of onion variety NUN 07212 ONL (e.g., as listed in Tables 1 and 2), with a different onion plant, and wherein one or more offspring of the crossing are subject to one or more plant breeding techniques: recurrent selection, backcrossing, pedigree breeding, mass selection, mutation breeding and genetic marker enhanced selection (see, e.g., Stein and Nothnagel, (1995) Plant Breeding 114, 1-11). For breeding methods in general, see, e.g., Principles of Plant Genetics and Breeding, 2007, George Acquaah, Blackwell Publishing, ISBN-13: 978-1-4051-3646-4.

In other aspects, the disclosure provides a progeny plant of onion variety NUN 07212 ONL, such as a progeny plant obtained by further breeding that variety. Further breeding with onion variety NUN 07212 ONL, includes selfing that variety and/or cross-pollinating that variety with another onion plant or variety one or more times. In a particular aspect, the disclosure provides for a progeny plant that retains all or all but one, two, or three of the morphological and physiological characteristics of onion variety NUN 07212 ONL, optionally all or all but one, two, or three characteristics as listed in Tables 1 and 2, determined at the 5% significance level for numerical characteristics and determined by type/degree for non-numerical characteristics, when grown under the same environmental conditions. In another aspect, the progeny is a first generation progeny, i.e., the ovule or the pollen (or both) used in the crossing is an ovule or pollen of onion variety NUN 07212 ONL, i.e., the pollen comes from an anther of onion variety NUN 07212 ONL and the ovule comes from an ovary of onion variety NUN 07212 ONL.

In another aspect, the plant and plant parts of onion variety NUN 07212 ONL and progeny of said variety are provided, e.g., grown from seeds, produced by sexual or vegetative reproduction, regenerated from the above-described plant parts, or regenerated from a cell or tissue culture of onion variety NUN 07212 ONL, in which the reproduced (seed propagated or vegetatively propagated) plant has all of the physiological and morphological characteristics of onion variety NUN 07212 ONL, e.g., as listed in Tables 1 and 2. In one aspect, said progeny of onion variety can be modified in one, two, or three characteristics, in which the modification is a result of mutagenesis or transformation with a transgene.

In one aspect, pedigree selection is used as a breeding method for developing an onion variety. Pedigree selection is also known as the "Vilmorin System of Selection," see, e.g., Allard, John Wiley & Sons, Inc., 1999, 64-67. In general, selection is first practiced among F2 plants. In the next season, the most desirable F3 lines are first identified, then desirable F3 plants within each line are selected. The following season and in all subsequent generations of inbreeding, the most desirable families are identified first, then desirable lines within the selected families are chosen. A family refers to lines that were derived from plants selected from the same progeny from the preceding generation.

Using pedigree method, two parents may be crossed using an emasculated female and a pollen donor (male) to produce F1 offspring. In order to optimize crossing, a method of misting may be used to wash the pollen off prior to fertilization to assure crossing or hybridization. The F1 may be self-pollinated to produce segregating F2 generation. Individual plants may then be selected which represent the desired phenotype in each generation (F3, F4, F5, etc.) until the traits are homozygous or fixed within a breeding population.

Thus, progeny in connection with pedigree selection are either the generation (seeds) produced from the first cross (F1) or selfing (S1), or any further generation produced by crossing and/or selfing (F2, F3, F4, F5, F6, F7, etc.) and/or backcrossing (BC1, BC2, BC3, BC4, BC5, BC6, BC7, etc.) one or more selected plants of the F1 and/or S1 and/or BC1 generation (or plants of any further generation, e.g., the F2) with another onion plant (an/or with wild relative of onion).

The disclosure also provides for a method of producing a new onion plant. The method comprises crossing a plant of onion variety NUN 07212 ONL, or a plant comprising all but 1, 2, or 3 of the morphological and physiological characteristics of said variety (e.g., as listed in Tables 1 and 2), or a progeny plant thereof, either as male or as female parent, with a second onion plant (or a wild relative of onion) one or more times, and/or selfing an onion plant of variety NUN 07212 ONL, or a progeny plant thereof, one or more times, and selecting progeny from said crossing and/or selfing. The second onion plant may, for example, be a line or variety of the species *Allium cepa*, or other *Allium* species.

In a further aspect, onion variety NUN 07212 ONL is used in crosses with other or different onion varieties to produce first generation (F1) onion hybrid seeds and plants with superior characteristics. In a particular aspect, the disclosure provides a method of producing a hybrid onion seed comprising crossing a first parent onion plant with a second parent onion plant and harvesting the resultant seed, in which the first parent onion plant or second parent onion plant is onion variety NUN 07212 ONL. Also provided is a hybrid onion seed produced from crossing a first parent onion plant with a second parent onion plant and harvesting the resultant hybrid onion seed, wherein said first parent onion plant or second parent onion plant is onion variety NUN 07212 ONL. In a further aspect, the hybrid onion plant produce from the hybrid onion seed is provided.

The morphological and physiological characteristics of onion variety NUN 07212 ONL are provided, for example, in Tables 1 and 2, as collected in a trial according to USDA and/or UPOV standards. Encompassed herein is also a plant obtainable from onion variety NUN 07212 ONL (e.g., by selfing and/or crossing and/or backcrossing with said variety and/or progeny of said variety) comprising all or all but one, two, or three of the physiological and morphological characteristics of onion variety NUN 07212 ONL listed in Tables 1 and 2 (e.g., determined at the 5% significance level for numerical characteristics and determined by type/degree for non-numerical characteristics) when grown under the same environmental conditions and/or comprising one or more (or all; or all except one, two, or three) characteristics when grown under the same environmental conditions. The morphological and/or physiological characteristics may vary somewhat with variation in the environment (e.g., temperature, light intensity, day length, humidity, soil, fertilizer use, disease vectors), which is why a comparison under the same environmental conditions is preferred. Colors can best be measured using Royal Horticultural Society (RHS) Chart.

In still another aspect, the disclosure provides a method of producing a plant derived from onion variety NUN 07212 ONL, the method comprising: (a) preparing a progeny plant derived from onion variety NUN 07212 ONL by crossing a plant of variety NUN 07212 ONL either as a male or female parent with a second plant or selfing onion variety NUN 07212 ONL or vegetative reproduction of onion variety NUN 07212 ONL, and (b) collecting seeds from said crossing or regenerating a whole plant from the vegetative cell- or tissue culture. Also provided are seeds and/or plants obtained by this method. All plants produced using onion variety NUN 07212 ONL as a parent are within the scope of the disclosure, including plant parts derived from onion variety NUN 07212 ONL.

In further aspects, the method comprises growing a progeny plant of a subsequent generation from said seed of a progeny plant of a subsequent generation and crossing the progeny plant of a subsequent generation with itself or a second plant and repeating the steps for an additional 3-10 generations to produce a plant derived from onion variety NUN 07212 ONL. The plant derived from onion variety NUN 07212 ONL may be an inbred line and the aforementioned repeating crossing steps may be defined as comprising sufficient inbreeding to produce the inbred line. By selecting plants having one or more desirable traits, a plant derived from onion variety NUN 07212 ONL is obtained which has some of the desirable traits of the line as well as potentially other selected traits.

The disclosure provides for methods of producing plants which retain all the morphological and physiological characteristics of a plant described herein. The disclosure provides also for methods of producing a plant comprising all but 1, 2, or 3 or more of the morphological and physiological characteristics of onion variety NUN 07212 ONL (e.g., as listed in Tables 1 and 2), but which are still genetically closely related to said onion variety. The relatedness can, for example, be determined by fingerprinting techniques (e.g., making use of isozyme markers and/or molecular markers such as Single-nucleotide polymorphism (SNP) markers, amplified fragment length polymorphism (AFLP) markers, microsatellites, minisatellites, Random Amplified Polymorphic DNA (RAPD) markers, restriction fragment length polymorphism (RFLP) markers and others). A plant is "closely related" to onion variety NUN 07212 ONL if its DNA fingerprint is at least 80%, 90%, 95% or 98% identical to the fingerprint of onion variety NUN 07212 ONL. In a particular aspect, AFLP markers are used for DNA fingerprinting (see, e.g., Vos et al. 1995, Nucleic Acid Research 23: 4407-4414). A closely related plant may have a Jaccard's Similarity index of at least about 0.8, preferably at least about 0.9, 0.95, 0.98 or more (see, e.g., Shim and Jorgensen, Theor Appl Genet (2000) 101:227-233). The disclosure also provides a plant and a variety obtained or selected by applying these methods on onion variety NUN 07212 ONL. Such a plant may be produced by traditional breeding techniques or mutation or transformation or in another aspect, a plant may simply be identified and selected amongst plants of said variety, or progeny of said variety, e.g., by identifying a variant within onion variety NUN 07212 ONL, which variant differs from the variety described herein in one, two, or three of the morphological and/or physiological characteristics (e.g., characteristics listed in Tables 1 and 2). In one aspect, the disclosure provides a plant of onion variety NUN 07212 ONL having a Jaccard's Similarity index with said variety of at least 0.8, e.g., at least 0.85, 0.9, 0.95, 0.98 or even at least 0.99.

In some aspects, the disclosure provides an onion plant comprising genomic DNA having at least 95%, 96%, 97%, 98% or 99% sequence identity compared to the genomic DNA sequence of a plant of onion variety NUN 07212 ONL, as deposited under Accession Number NCIMB 43755. In some aspects, the onion plant further comprises all or all but 1, 2, or 3 of the morphological and physiological characteristics of onion variety NUN 07212 ONL (e.g., as listed in Tables 1 and 2). In other aspects, the onion plant is a hybrid derived from a seed or plant of onion variety NUN 07212 ONL.

For the purpose of this disclosure, the "sequence identity" of nucleotide sequences, expressed as a percentage, refers to the number of positions in the two optimally aligned sequences which have identical residues (×100) divided by the number of positions compared. A gap, i.e., a position in the pairwise alignment where a residue is present in one sequence but not in the other, is regarded as a position with non-identical residues. A pairwise global sequence alignment of two nucleotide sequences is found by aligning the two sequences over the entire length according to the Needleman and Wunsch global alignment algorithm described in Needleman and Wunsch, 1970, J. Mol. Biol. 48(3):443-53). A full implementation of the Needleman-Wunsch global alignment algorithm is found in the needle program in The European Molecular Biology Open Software Suite (see, e.g., EMBOSS, Rice et al., Trends in Genetics June 2000, vol. 16, No. 6. pp. 276-277).

In one aspect, the plant of onion variety NUN 07212 ONL may also be mutated (by e.g., irradiation, chemical mutagenesis, heat treatment, etc.) and mutated seeds or plants may be selected in order to change one or more characteristics of said variety. Methods such as TILLING (Targeting Induced Local Lesions in Genomes) may be applied to onion populations in order to identify mutants.

Similarly, onion variety NUN 07212 ONL may be transformed and regenerated, whereby one or more chimeric genes are introduced into the variety or into a plant comprising all but 1, 2, 3, or more of the morphological and physiological characteristics (e.g., as listed in Tables 1 and 2). Many useful traits can be introduced into onion variety NUN 07212 ONL by e.g., crossing onion variety NUN 07212 ONL with a transgenic onion plant comprising a desired transgene as well as by directly introducing a transgene into onion variety NUN 07212 ONL by genetic transformation techniques.

Any pest or disease resistance genes may be introduced into onion variety NUN 07212 ONL, progeny of said variety or into a plant comprising all but 1, 2, or 3 or more of the morphological and physiological characteristics of onion variety NUN 07212 ONL (e.g., as listed in Tables 1 and 2). Resistance to one or more of the following diseases or pests may be introduced into plants described herein: Downey Mildew (*Peronospora destructor*), *Botrytis* Leaf Blight (*Botrytis squamosa*), Purple Blotch (*Stemphylium vesicarium*), *Fusarium* Basal Rot (*Fusarium oxysporum* f. sp. *cepae*), Pink Root (*Phoma terrestris*), White Rot (*Sclerotium cepivorum* Berk.), Black mold (*Aspergilis niger*), Neck Rot (*Botrytis allii*), Blue Mold (*Penicillium hirsutum*), Thrips (*Thrips tabaci*), Bulb Nematode (*Ditylenchus dipsaci*), and Root Knot Nematodes (*Meloidogyne* spp.). Other resistances, against pathogenic viruses (e.g., Iris Yellow Spot Virus), fungi, bacteria, nematodes, insects or other pests may also be introduced.

Genetic transformation may, therefore, be used to insert a selected transgene into the onion plants of the disclosure described herein or may, alternatively, be used for the preparation of transgenic onion plants which can be used as a source of transgene(s), which can be introduced into onion variety NUN 07212 ONL by e.g., backcrossing. A genetic trait which has been engineered into the genome of a particular onion plant may then be moved into the genome of another onion plant (e.g., another variety) using traditional breeding techniques which are well known in the art. For example, backcrossing is commonly used to move a transgene from a transformed onion variety into an already developed onion variety and the resulting backcross conversion plant will then comprise the transgene(s).

Any DNA sequences, whether from a different species or from the same species, which are inserted into the genome using transformation, are referred herein collectively as "transgenes". A "transgene" also encompasses antisense, or sense and antisense sequences capable of gene silencing. Thus, the disclosure also related to transgenic plants of onion variety NUN 07212 ONL. In some aspects, a transgenic plant of onion variety NUN 07212 ONL may contain at least one transgene but could also contain at least 1, 2, 3, 4, or more transgenes.

Plant transformation involves the construction of an expression vector which will function in plant cells. Such a vector comprises DNA comprising a gene under control of, or operatively linked to a regulatory element active in plant cells (e.g., promoter). The expression vector may contain one or more such operably linked gene/regulatory element combinations. The vector may be in the form of a plasmid and can be used alone or in combination with other plasmids to provide transformed onion plants using transformation methods to incorporate transgenes into the genetic material of the onion plant(s). Transformation can be carried out using standard methods, such as *Agrobacterium tumefaciens* mediated transformation or biolistics, followed by selection of the transformed cells and regeneration into plants.

Plants can also be genetically engineered, modified, or manipulated to express various phenotypes of horticultural interest. Through the transformation of onion, the expression of genes can be altered to enhance disease resistance, insect resistance, herbicide resistance, stress tolerance, horticultural quality, and other traits. Transformation can also be used to insert DNA sequences which control or help control male sterility or fertility restoration. DNA sequences native to onion as well as non-native DNA sequences can be transformed into onion and used to alter levels of native or non-native traits. Various promoters, targeting sequences, enhancing sequences, and other DNA sequences can be inserted into the genome for the purpose of altering the expression of proteins. Reduction of activity of specific genes (also known as gene silencing or gene suppression) is desirable for several aspects of genetic engineering in plants.

Genome editing is another method recently developed to genetically engineer plants. Specific modification of chromosomal loci or targeted mutation can be done through sequence-specific nucleases (SSNs) by introducing a targeted DNA double strand break in the locus to be altered. Examples of SSNs that have been applied to plants are: finger nucleases (ZFNs), transcription activator-like effector nucleases (TALENs), engineered homing endonucleases or meganucleases, and clustered regularly interspaced short palindromic repeats (CRISPR)/CRISPR-associated protein 9 (Cas9), see, e.g., Songstad, et. al., Critical Reviews in Plant Sciences, 2017, 36:1, 1-23.

Thus, the disclosure provides a method of producing an onion plant having a desired trait, comprising mutating a plant or plant part of onion variety NUN 07212 ONL, optionally with a target gene, and selecting a plant with the desired trait, wherein the mutated plant or part thereof retains all or all but one, two, or three of the physiological and morphological characteristics of said onion variety, optionally as described in Tables 1 and 2, and contains the desired trait and wherein a representative sample of seed of onion variety NUN 07212 ONL has been deposited under Accession Number NCIMB 43755. In a further aspect, the desired trait is yield, size, shape, color, flavor, storage properties, nutritional quality, post-harvest quality, male sterility, herbicide tolerance, insect resistance, pest resistance, disease resistance, environmental stress tolerance, modified carbohydrate metabolism, or modified protein metabolism.

The disclosure also provides a method for inducing a mutation in onion variety NUN 07212 ONL comprising:
  a. exposing the seed, plant, plant part, or cell of onion variety NUN 07212 ONL to a mutagenic compound or to radiation, wherein a representative sample of seed of onion variety NUN 07212 ONL is deposited under Accession Number NCIMB 43755;
  b. selecting the seed, plant, plant part, or cell of onion variety NUN 07212 ONL having a mutation; and
  c. optionally growing and/or multiplying the seed, plant, plant part, or cell of NUN 07212 ONL having the mutation.

The disclosure also provides a method of producing an onion plant having a desired trait, wherein the method comprises transforming the onion plant with a transgene that confers the desired trait, wherein the transformed plant otherwise retains all of the physiological and morphological characteristic of the plant of variety NUN 07212 ONL and contains the desired trait. Thus, a transgenic onion plant is provided which is produced by the method described above, wherein the plant comprises the desired trait and has all of the physiological and morphological characteristics of onion variety NUN 07212 ONL.

In another aspect, the disclosure provides a method of producing a progeny of plant of variety NUN 07212 ONL further comprising a desired trait, said method comprising transforming the plant of onion variety NUN 07212 ONL with at least one transgene that confers the desired trait and/or crossing the plant of onion variety NUN 07212 ONL with a transgenic onion plant comprising a desired transgene so that the genetic material of the progeny that resulted from the cross contains the desired transgene(s). Also encompassed is the progeny produced by this method.

A desired trait (e.g., gene(s)) conferring pest or disease resistance, herbicide, fungicide or insecticide tolerance, etc.) can be introduced into onion variety NUN 07212 ONL, or progeny of said variety, by transforming said variety or progeny of said variety with a transgene that confers the desired trait, wherein the transformed plant retains all or all but one, two, or three of the physiological and/or morphological and/or physiological characteristics of onion variety NUN 07212 ONL or the progeny of said variety and contains the desired trait. In another aspect, the transformation or mutation confers a trait wherein the trait yield, size, shape, color, flavor or taste, storage properties, nutritional quality, post-harvest quality, male sterility, herbicide tolerance, insect resistance, pest resistance, disease resistance, environmental stress tolerance, modified carbohydrate metabolism, modified protein metabolism, or ripening. In a particular aspect, the specific transgene may be any known in the art or listed herein, including, a polynucleotide sequence conferring resistance to imidazolinone, sulfonylurea, glyphosate, glufosinate, triazine, benzonitrile, cyclohexanedione, phenoxy proprionic acid and L-phosphinothricin or a polynucleotide conferring resistance to Downey Mildew (*Peronospora destructor*), *Botrytis* Leaf Blight (*Botrytis squamosa*), Purple Blotch (*Stemphylium vesicarium*), *Fusarium* Basal Rot (*Fusarium oxysporum* f. sp. *cepae*), Pink Root (*Phoma terrestris*), White Rot (*Sclerotium cepivorum* Berk.), Black mold (*Aspergilis niger*), Neck Rot (*Botrytis allii*), Blue Mold (*Penicillium hirsutum*), Thrips (*Thrips tabaci*), Bulb Nematode (*Ditylenchus dipsaci*), and Root Knot Nematodes (*Meloidogyne* spp.). Other resistances, against pathogenic viruses (e.g., Iris Yellow Spot Virus), fungi, bacteria, nematodes, insects or other pests may also be introduced.

By crossing and/or selfing, (one or more) single traits may be introduced into the onion variety NUN 07212 ONL (e.g., using backcrossing breeding schemes), while retaining the remaining morphological and physiological characteristics of said variety and/or while retaining one or more or all distinguishing characteristics. A single trait converted plant may thereby be produced. For example, disease resistance genes may be introduced, genes responsible for one or more quality traits, yield, etc. Both single genes (e.g., dominant or recessive) and one or more QTLs (quantitative trait loci) may be transferred into NUN 07212 ONL by breeding with said variety.

In another aspect, the disclosure provides a method of introducing a single locus conversion, single trait conversion, or a desired trait into onion variety NUN 07212 ONL, comprising introducing a single locus conversion, single trait conversion, or a desired trait in at least one of the parents of onion variety NUN 07212 ONL, and crossing the converted parent with the other parent of onion variety NUN 07212 ONL to obtain seed of said onion variety.

In another method, the step of introducing a single locus conversion, single trait conversion, or a desired trait in at least one of the parent plants comprises:
  a. crossing the parental line of onion variety NUN 07212 ONL with a second onion plant comprising the single locus conversion, the single trait conversion or the desired trait;
  b. selecting F1 progeny plants that contain the single locus conversion, the single trait conversion or the desired trait;
  c. crossing said selected progeny plants of step b) with the parental line of step a), to produce a backcross progeny plant;
  d. selecting backcross progeny plants comprising the single locus conversion, the single trait conversion or the desired trait and otherwise all or all but one, two or three of the morphological and physiological characteristics the parental line of step a) to produce selected backcross progeny plants; and
  e. optionally repeating steps c) and d) one or more times in succession to produce selected second, third or fourth or higher backcross progeny plants comprising the single locus conversion, the single trait conversion or the desired trait and otherwise all or all but one, two, or three of the morphological and physiological characteristics the parental line of step a) to produce selected backcross progeny plants, when grown in the same environmental conditions.

The disclosure further relates to plants obtained by this method.

In another aspect, introducing a single locus conversion, a single trait conversion, or a desired trait in at least one of the parents comprise:
  a. obtaining a cell or tissue culture of cells of the parental line of onion variety NUN 07212 ONL;
  b. genetically transforming or mutating said cells;
  c. growing the cells into a plant; and
  d. optionally selecting plants that contain the single locus conversion, the single trait conversion, or the desired trait.

In another aspect, the disclosure provides a method of introducing a single locus conversion, a single trait conversion, or a desired trait into onion variety NUN 07212 ONL comprising:
  a. obtaining a combination of a parental lines of onion variety NUN 07212 ONL, optionally through reverse synthesis of breeding lines;
  b. introducing a single locus conversion, a single trait conversion, or a desired trait in at least one of the parents of step a; and
  c. crossing the converted parent with the other parent of step a to obtain seed of onion variety NUN 07212 ONL.

In any of the above methods, wherein the single locus conversion concerns a trait, the trait may be yield or pest resistance or disease resistance. In one aspect, the trait is disease resistance and the resistance is conferred Downey Mildew (*Peronospora destructor*), *Botrytis* Leaf Blight (*Botrytis squamosa*), Purple Blotch (*Stemphylium vesicarium*), *Fusarium* Basal Rot (*Fusarium oxysporum* f. sp. *cepae*), Pink Root (*Phoma terrestris*), White Rot (*Sclerotium cepivorum* Berk.), Black mold (*Aspergilis niger*), Neck Rot (*Botrytis allii*), Blue Mold (*Penicillium hirsutum*), Thrips (*Thrips tabaci*), Bulb Nematode (*Ditylenchus dipsaci*), and Root Knot Nematodes (*Meloidogyne* spp.). Other resistances, against pathogenic viruses (e.g., Iris Yellow Spot Virus), fungi, bacteria, nematodes, insects or other pests may also be introduced.

The disclosure also provides a plant having one, two, or three physiological and/or morphological characteristics which are different from those of onion variety NUN 07212 ONL and which otherwise has all the physiological and morphological characteristics of said onion variety, wherein a representative sample of seed of onion variety NUN 07212 ONL has been deposited under Accession Number NCIMB 43755. In particular, variants which differ from onion variety NUN 07212 ONL in none, one, two or three of the characteristics mentioned in Tables 1 and 2 are encompassed.

The disclosure also provides an onion plant comprising at least a first set of the chromosomes of onion variety NUN 07212 ONL, a sample of seed of said onion variety has been deposited under Accession Number NCIMB 43755; optionally further comprising a single locus conversion, wherein said plant has essentially all of the morphological and physiological characteristics of the plant comprising at least a first set of the chromosomes of said variety. In another aspect, this single locus conversion confers yield, size, shape, color, flavor or taste, storage properties, nutritional quality, post-harvest quality, male sterility, herbicide tolerance, insect resistance, pest resistance, disease resistance, environmental stress tolerance, modified carbohydrate metabolism, modified protein metabolism, or ripening.

In one aspect, the disclosure provides a haploid plant and/or a doubled haploid plant of onion variety NUN 07212 ONL, or of a plant having all but one, two, or three physiological and/or morphological characteristics of onion variety NUN 07212 ONL, or progeny of said onion variety. Haploid and doubled haploid (DH) plants can, for example, be produced by cell or tissue culture and chromosome doubling agents and regeneration into a whole plant. DH production chromosome doubling may be induced using known methods, such as colchicine treatment or the like. In one aspect, the method comprises inducing a cell or tissue culture with chromosome doubling agent and regenerating the cells or tissues into a whole plant.

In another aspect, the disclosure comprises method for making doubled haploid cells of onion variety NUN 07212 ONL, comprising making doubled haploid cells from haploid cells from the plant or plant part of onion variety NUN 07212 ONL with a chromosome doubling agent, such as colchicine treatment (see, e.g., Nikolova and Niemirowicz-Szczytt (1996) Acta Soc Bot Pol 65:311-317).

In another aspect, the disclosure provides haploid plants and/or doubled haploid plants derived from onion variety NUN 07212 ONL that, when combined, make a set of parents of onion variety NUN 07212 ONL. The haploid plant and/or the doubled haploid plant of onion variety NUN 07212 ONL can be used in a method for generating parental lines of onion variety NUN 07212 ONL.

The disclosure relates to a method of producing a combination of parental lines of a plant of onion variety NUN 07212 ONL, comprising the step of making doubled haploid cells from haploid cells from said plant or a seed of that plant; and optionally crossing these parental lines to produce and collect seeds. In another aspect, the disclosure relates to a combination of parental lines produced by this method. In still another aspect, the combination of parental lines can be used to produce a seed or plant of onion variety NUN 07212 ONL when these parental lines are crossed. In still another aspect, the disclosure relates to a combination of parental lines from which a seed or plant having all physiological and/or morphological characteristics of onion variety NUN 07212 ONL (e.g., determined at the 5% significance level for numerical characteristics and determined by type/degree for non-numerical characteristics) when grown under the same conditions.

In another aspect, a combination of a male and a female parental line of onion variety NUN 07212 ONL can be generated, for example, through reverse synthesis of breeding lines.

Using methods known in the art like "reverse synthesis of breeding lines" or "reverse breeding," it is possible to produce parental lines for a hybrid plant such as onion variety NUN 07212 ONL. A skilled person can take any individual heterozygous plant (called a "phenotypically superior plant" in Example 2 of US 2015/0245570; which is hereby incorporated by reference in its entirety; onion variety NUN 07212 ONL is such a plant) and generate a combination of parental lines (reverse breeding parental lines) that, when crossed, produce the variety NUN 07212 ONL. It is not necessary that the reverse breeding parental lines are identical to the original parental lines. Such new breeding methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from US 2015/0245570 or from Wijnker et al., Nature Protocols Volume: 9, Pages: 761-772 (2014) DOI: doi:10.1038/nprot.2014.049. Thus, the disclosure provides a method for producing parental lines for a hybrid organism (e.g., onion variety NUN 07212 ONL), comprises in one aspect: a) defining a set of genetic markers that are present in a heterozygous form (H) in a partially heterozygous starting organism; b) producing doubled haploid lines from spores of the starting organism: c) genetically characterizing the doubled haploid lines thus obtained for the said set of genetic markers to determine whether they are present in a first homozygous form (A) or in a second homozygous form (B); and d) selecting at least one pair of doubled haploid lines that have complementary alleles for at least a subset of the genetic markers, wherein each member of the pair is suitable as a parental line for a hybrid organism.

In another aspect, the method for producing parental lines for hybrid organisms, e.g., of onion variety NUN 07212 ONL, which when crossed reconstitute the genome of onion variety NUN 07212 ONL, comprising:
  a. defining a set genetic markers that are present a heterozygous form (H) in a partially heterozygous starting organism;
  b. producing at least one further generation from the starting organism by self-pollination (e.g., F2 or F3 generation);
  c. selecting at least one pair of progeny organisms in which at least one genetic marker from the set is present in a complementary homozygous form (B vs. A, or A vs. B); and
  d. optionally repeating steps b) and c) until at least one pair of progeny organisms that have complementary alleles for at least a subset of the genetic markers had been selected as parental lines for a hybrid.

The disclosure also provides methods for determining the identity of parental lines described herein, in particular the identity of the female line. US 2015/0126380, which is incorporated by reference, relates to a non-destructive method for analyzing maternal DNA of a seed. In this method, the DNA is dislodged from the seed coat surface and can be used to collect information on the genome of the maternal parent of the seed. This method for analyzing maternal DNA of a seed comprises the steps of contacting a seed with a fluid to dislodge DNA from the seed coat surface, and analyzing the DNA thus dislodged from the seed coat surface using methods known in the art. The skilled person is thus able to determine whether a seed has grown on a plant of a plant onion variety NUN 07212 ONL, or is a progeny of said variety, because the seed coat of the seed is a maternal tissue genetically identical to onion variety NUN 07212 ONL. In one aspect, the disclosure relates to an onion seed coat comprising maternal tissue of onion variety NUN 07212 ONL. In another particular aspect, the disclosure provides a method of identifying the female parental line of onion variety NUN 07212 ONL by analyzing the seed coat or another maternal tissue of said seed.

In another aspect, the disclosure provides a method of determining the genotype of a plant of the disclosure comprising the step of detecting in the genome (e.g., a sample of nucleic acids) of the plant at least a first polymorphism or an allele. The skilled person is familiar with many suitable methods of genotyping, detecting a polymorphism or detecting an allele including restriction fragment length polymorphism identification (RFLP) of genomic DNA, random amplified polymorphic detection (RAPD) of genomic DNA, amplified fragment length polymorphism detection (AFLP), polymerase chain reaction (PCR), DNA sequencing, allele specific oligonucleotide (ASO) probes, and hybridization to DNA microarrays or beads. Alternatively, the entire genome could be sequenced. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium.

Also provided is a plant part obtainable from onion variety NUN 07212 ONL or from progeny of said variety or from a plant having all but one, two, or three physiological and/or morphological characteristics which are different from those of onion variety NUN 07212 ONL, or from a vegetatively propagated plant of onion variety NUN 07212 ONL (or from its progeny or from a plant having all or all but one, two, or three physiological and/or morphological characteristics which are different from those of onion variety NUN 07212 ONL), wherein said plant part is a bulb, or a part of a bulb, a leaf, a part of a leaf, pollen, an ovule, a cell, a petiole, a shoot or a part thereof, a stem or a part thereof, a cutting, a seed, a part of a seed, seed-coat or another maternal tissue which is part of a seed grown on onion variety NUN 07212 ONL, or a hypocotyl, a cotyledon, a pistil, an anther, or a flower or a part thereof.

Such a plant part of onion variety NUN 07212 ONL can be stored and/or processed further. The disclosure also provides for a food or feed products comprising one or more of such parts, such as canned, chopped, cooked, roasted, in a sauce, in a sandwich, pasted, puréed or concentrated, juiced, frozen, dried, pickled, or powdered onion from onion variety NUN 07212 ONL or from progeny of said variety, or from a derived variety, such as a plant having all but one, two, or three physiological and/or morphological characteristics of onion variety NUN 07212 ONL. Preferably, the plant part is an onion bulb or part thereof and/or an extract from a bulb or another plant part described herein comprising at least one cell of onion variety NUN 07212 ONL. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen.

In another aspect, the disclosure provides for an onion bulb of variety NUN 07212 ONL, or a part of a bulb of said variety. The bulb can be in any stage of maturity, for example, immature or mature.

In another aspect, the disclosure provides for a container comprising or consisting of a plurality of harvested onion bulbs or parts of bulbs of said variety, or bulbs of progeny thereof, or bulbs of a derived variety.

Marketable onion bulbs are generally sorted by size and quality after harvest. Alternatively, onion bulbs can be sorted by pungency.

Also, at-harvest and/or post-harvest characteristics of bulbs can be compared, such as storage holding quality, skin color, and scale retention.

In another aspect, the plant, plant part, or seed of onion variety NUN 07212 ONL is inside one or more containers. For example, the disclosure provides containers such as cans, boxes, crates, bags, cartons, Modified Atmosphere Packaging, films (e.g., biodegradable films), etc. comprising a plant or a part of a plant (fresh and/or processed) or a seed of onion variety NUN 07212 ONL. In a particular aspect, the container comprises a plurality of seeds of onion variety NUN 07212 ONL, or a plurality of plant parts of onion variety NUN 07212 ONL. The seed may be disinfected, primed and/or treated with various compounds, such as seed coatings or crop protection compounds. The seed produces a plant of onion variety NUN 07212 ONL.

All documents (e.g., patent publications) are herein incorporated by reference in their entirety, including the following cited references:

Naktuinbow, Calibration book *Daucuc carota* L, 2010.
UPOV, "Guidelines for the Conduct of Tests for Distinctness, Uniformity and Stability, TG/49/8 (Geneva 2007, last updated in 2015-03-25), world-wide web at upov.int under edocs/tgdocs/en/tg049.pdf.
US Department of Agriculture, Agricultural Marketing Service, "Objective description of Variety—Onion (*Daucus carota*)," world wide web at ams.usda.gov/services/plant-variety-protection/pvpo-c-forms, under onion.
Arnhold-Schmitt, B., et. al., "Physiological Aspects of Genome Variability in Tissue Culture. I. Growth Phase-Dependent Differential DNA Methylation of the Onion Genome (*Daucus carota* L.) During Primary Culture", Theoretical and Applied Genetics, 1995, vol. 91, no. 5, pp. 809-815
Jhang, T., et. al., "Efficiency of Different Marker Systems for Molecular Characterization of Subtropical Onion Germplasm," The Journal of Agricultural Science, 2010, vol. 148, no. 2, pp. 171-181.
Larkin, P. J., et. al., "Somaclonal Variation—A Novel Source of Variability from Cell Cultures for Plant Improvement", Theoretical and Applied Genetics, 1981, vol. 60, no. 4, pp. 197-214.
Martin, E., et al., "Identification of Markers Linked to Agronomic Traits in Globe Artichoke", Australian Journal of Crop Science, 2008, vol. 1(2), pp. 43-46.
Needleman, S. B., et. al., "A General Method Applicable to the Search for Similarities in the Amino Acid Sequence of Two Proteins", Journal of Molecular Biology, 1970, vol. 48(3), pp. 443-53.
Nikolova, V., et. al., "Diploidization of Cucumber (*Cucumis sativus* L.) Haploids by Colchini Treatment", Acta Societas Botanicorum Poloniae, 1996, vol. 65, pp. 311-317.
Nuñez, et. al., "Onion Production in California," University of California Agriculture and Natural Resources Communication Services, Publication 7226, 1997, pp. 1-5.
Rice, P., et al., "EMBOSS: The European Molecular Biology Open Software Suite", Trends in Genetics, 2000, vol. 16, Issue 6. pp. 276-277.
Shim, S. J., and Jorgensen, R. B., "Genetic Structure in Cultivated and Wild Onions (*Daucus carota* L.) Revealed by AFLP Analysis", Theor Appl Genet, 2000, vol. 101, pp. 227-233.
Stein, M., et. al., "Some Remarks on Onion Breeding (*Daucus carota saativus* Hoffm.), Plant Breeding, 1995, vol. 114, no. 1, pp. 1-11.
Vos, P., et al., "AFLP: A New Technique for DNA Fingerprinting", Nucleic Acids Research, 1995, vol. 23(21), pp. 4407-4414.
Voss, R. E. et. al., "Fresh Market Bulb Onion Production in California," University of California Agriculture and Natural Resources Communication Services, ISBN 978-1-60107-033.3, pp. 1-4.
Wijnker, E., et al., "Hybrid Recreation by Reverse breeding in *Arabidopsis thaliana*", Nature Protocols, 2014, vol. 9, pp. 761-772. DOI: doi: 10.1038/nprot.2014.049
US 2015/0126380
US 2015/0245570

Development of Onion Variety NUN 07212 ONL

The hybrid onion variety NUN 07212 ONL was developed from a male and female proprietary inbred line of Nunhems. The female and male parents were crossed to produce hybrid (F1) seeds of onion variety NUN 07212 ONL. The seeds of onion variety NUN 07212 ONL can be grown to produce hybrid plants and parts thereof (e.g., onion bulbs). The hybrid onion variety NUN 07212 ONL can be propagated by seeds or vegetatively.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant has concluded that onion variety NUN 07212 ONL is uniform and stable.

Deposit Information

A total of 625 seeds of the hybrid onion variety NUN 07212 ONL was made and accepted according to the Budapest Treaty by Nunhems B.V. on Dec. 1, 2021 at NCIMB Ltd., Ferguson Building, Craibstone Estate, Bucksburn, Aberdeen AB21 9YA, United Kingdom (NCIMB). The deposit has been assigned NCIMB number 43755. A statement indicating the viability of the sample has been provided. A deposit of onion variety NUN 07212 ONL and of the male and female parent line is also maintained at Nunhems B.V. The seed lot number for onion variety NUN 07212 ONL is 25572601009.

The deposit will be maintained in NCIMB for a period of 30 years, or 5 years after the most recent request, or for the enforceable life of the patent whichever is longer and will be replaced if it ever becomes nonviable during that period.

Access to the deposits will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. Applicant does not waive any rights granted under this patent on this application or under the Plant Variety Protection Act (7 U.S.C. § 2321 et seq.). Accordingly, the requirements of 37 CFR § 1.801-1.809 have been satisfied.

Characteristics of Onion Variety NUN 07212 ONL

The most similar variety to NUN 07212 ONL is referred to as variety NUN 07206 ONL a commercial variety from Nunhems B.V. with commercial name Airoso. See U.S. Pat. No. 10,285,361 ("Hybrid onion variety NUN 07206").

In Tables 1 and 2, a comparison between onion variety NUN 07212 ONL and the Reference Variety is shown based on a trial in the Pacific Northwest, USA in 2021.

One replication of 20 plants per variety, from which at least 15 plants or plant parts were randomly selected and were used to measure characteristics. For numerical characteristics, averages were calculated. For non-numerical characteristics, the type/degree were determined. Similarity and differences between two different plant lines or varieties can be determined by comparing the number of morphological and/or physiological characteristics (e.g., characteristics as listed in Tables 1 and 2) that are the same (i.e., statistically not significantly different) or that are different (i.e., statistically significantly different) between the two plant lines or varieties using plants grown under the same environmental conditions. A numerical characteristic is considered to be "the same" when the value for a numeric characteristic is not significantly different at the 1% (p<0.01) or 5% (p<0.05) significance level, using T-test, a standard method known to the skilled person. A non-numerical or "degree" or "type" characteristic is considered "the same" when the values have the same "degree" or "type" when scored using USDA and/or UPOV descriptors, for plants are grown under the same environmental conditions. In one aspect, a statistical analysis using the T-Test at 5% significance level is provided (see, Tables 4-8).

In one aspect, the disclosure provides a plant having the physiological and morphological characteristics of onion variety NUN 07212 ONL as presented in Tables 1 and 2 when grown under the same environmental conditions.

TABLE 1

Objective Description of Onion Variety NUN 07212 ONL and the Reference Variety (USDA Descriptors)

| Characteristics | Application Variety (NUN 07212 ONL) | Reference Variety (NUN 07206 ONL) |
|---|---|---|
| Type: | | |
| Bulb, Bunching | Bulb | Bulb |
| Short day, Long day | Long day | Long day |
| Maturity: | Early | Early |
| early, medium, late | | |
| Areas of adaptation: | Pacific Northwest, USA Nevada & Northern USA | Pacific Northwest, USA Nevada & Northern USA |
| Plant: | | |
| Height above soil line to highest point of any foliage, cm: | 33.30 cm | 33.97 cm |
| Habit: | Erect | Intermediate |
| erect, intermediate, floppy | | |
| Leaf: | | |
| Color: | Dark green | Medium green |
| light green, medium green, blue green | | |
| Bulb: | | |
| Size (harvest): | Large Jumbo | Large Jumbo |
| small, medium, large | | |
| Shape: | Globe | Globe |
| globe, deep globe, fit globe, top shape, deep flat, thick flat, flat, torpedo-long oval | | |
| Height, mm: | 84.14 mm | 90.20 mm |
| Diameter, mm: | 87.51 mm | 77.73 mm |
| Shape index (average height/average diameter): | 0.96 | 1.16 |
| Color (skin): | Golden Brown RHS 173 C | Golden Brown RHS 173D |
| brown, purplish red, buff red, pinkish yellow, brownish yellow, deep yellow, medium yellow, pale yellow, white, other | | |
| Color (interior): | White RHS 158D | White RHS 158C |
| pink, red, purplish red, white, cream, light green-yellow, dark green-yellow | | |
| Scales: | Medium | Medium |
| few, medium, many | | |
| Scales: | Medium | Medium |
| thick, medium, thin | | |
| Scale retention: | Good | Good |
| very good, good, good, poor | | |

TABLE 1-continued

Objective Description of Onion Variety NUN 07212
ONL and the Reference Variety (USDA Descriptors)

| Characteristics | Application Variety (NUN 07212 ONL) | Reference Variety (NUN 07206 ONL) |
|---|---|---|
| Pungence: mild, medium, strong | Medium | Medium |
| Storage: good, fair, poor | Very good | Very good |
| Bulb weight, g: | 348.80 g | 274.27 g |

TABLE 2

Objective Description of Onion Variety NUN 07212 ONL
and the Reference Variety (Non-USDA Descriptors)

| Characteristics | Application Variety (NUN 07212 ONL) | Reference Variety (NUN 07206 ONL) |
|---|---|---|
| Leaf: | | |
| Foliage - attitude: | Erect | Semi-erect |
| Foliage - waxiness: | Medium | Medium |
| Foliage - intensity of green color: | Dark | Medium |
| Foliage - cranking: | Absent or weak | Intermediate |
| Pseudostem: | | |
| Length (up to highest green leaf): | Long | Long |
| Length, mm: | 63.38 mm | 70.93 mm |
| Bulb: | | |
| Onion size: | Large | Large |
| Onion height: | Medium | Medium to tall |
| Onion diameter: | Large | Medium |
| Height/diameter: | Medium | Large |
| Position at maximum diameter: | At middle | At middle |
| Width of neck: | Medium | Medium |
| Bulb shape in longitudinal section: | Circular | Broad obovate |
| Shape of stem end: | Rounded | Slightly sloping |
| Shape of root end: | Flat | Round |
| Adherence of dry skin after harvest: | Medium | Medium |
| Thickness of dry skin: | Medium to thick | Medium |
| Base color of dry skin: | Brown | Brown |
| Intensity of base color of dry skin: | Medium | Medium |
| Hue of color of dry skin: | Absent | Absent |
| Coloration of epidermis of fleshy scales: | Absent | Absent |

TABLE 3

Distinguishing Characteristics of Onion Variety
NUN 07212 ONL and the Reference Variety

| Characteristics | Application Variety (NUN 07212 ONL) | Reference Variety (NUN 07206 ONL) |
|---|---|---|
| Plant: | | |
| Habit: erect, intermediate, floppy | Erect | Intermediate |
| Leaf: | | |
| Color: light green, medium green, blue green | Dark green | Medium green |
| Foliage - attitude: | Erect | Semi-erect |
| Foliage - intensity of green color: | Dark | Medium |
| Foliage - cranking: | Absent or weak | Intermediate |
| Bulb: | | |
| Height, mm: | 84.14 mm | 90.20 mm |
| Onion height: | Medium | Medium to tall |
| Diameter, mm: | 87.51 mm | 77.73 mm |

TABLE 3-continued

Distinguishing Characteristics of Onion Variety
NUN 07212 ONL and the Reference Variety

| Characteristics | Application Variety (NUN 07212 ONL) | Reference Variety (NUN 07206 ONL) |
| --- | --- | --- |
| Onion diameter: | Large | Medium |
| Height/diameter: | Medium | Large |
| Color (skin): brown, purplish red, buff red, pinkish yellow, brownish yellow, deep yellow, medium yellow, pale yellow, white, other | Golden Brown RHS 173 C | Golden Brown RHS 173D |
| Color (interior): pink, red, purplish red, white, cream, light green-yellow, dark green-yellow | White RHS 158D | White RHS 158C |
| Bulb weight, g: | 348.80 g | 274.27 g |
| Bulb shape in longitudinal section: | Circular | Broad obovate |
| Shape of stem end: | Rounded | Slightly sloping |
| Shape of root end: | Flat | Round |
| Thickness of dry skin: | Medium to thick | Medium |

The result of the T-Test shows significant difference at 5% significance level between onion variety NUN 07212 ONL and the Reference Variety for bulb height, bulb diameter, and bulb weight as shown in Tables 4-6.

Table 4 shows a significant difference at 5% significance level between onion variety NUN 07212 ONL and the Reference Variety (p=0.016) for bulb height (mm) based on a trial in the US in 2021.

TABLE 4

| Statistical Parameter | Application Variety NUN 07212 ONL | Reference Variety NUN 07206 ON |
| --- | --- | --- |
| No. of samples | 15 | 15 |
| Minimum | 69.90 | 81.0 |
| Maximum | 89.98 | 107.65 |
| Median | 85.76 | 87.58 |
| Mean | 84.14 | 90.20 |
| Standard deviation | 5.24 | 7.53 |

Table 5 shows a significant difference at 5% significance level between onion variety NUN 07212 ONL and the Reference Variety (p<0.001) for bulb diameter (mm) based on a trial in the US in 2021.

TABLE 5

| Statistical Parameter | Application Variety NUN 07212 ONL | Reference Variety NUN 07206 ON |
| --- | --- | --- |
| No. of samples | 15 | 15 |
| Minimum | 80.26 | 70.55 |
| Maximum | 96.89 | 83.73 |
| Median | 87.08 | 77.70 |
| Mean | 87.51 | 77.73 |
| Standard deviation | 5.51 | 3.98 |

Table 6 shows a significant difference at 5% significance level between onion variety NUN 07212 ONL and the Reference Variety (p=0.001) for bulb weight (g) based on a trial in the US in 2021.

TABLE 6

| Statistical Parameter | Application Variety NUN 07212 ONL | Reference Variety NUN 07206 ON |
| --- | --- | --- |
| No. of samples | 15 | 15 |
| Minimum | 234.0 | 202.0 |
| Maximum | 450.0 | 362.0 |
| Median | 364.0 | 268.0 |
| Mean | 348.80 | 247.24 |
| Standard deviation | 59.65 | 43.94 |

The result of the T-Test shows no significant difference at 5% significance level between onion variety NUN 07212 ONL and the Reference Variety for plant height and pseudo stem length as shown in Tables 7-8.

Table 7 shows no significant difference at 5% significance level between onion variety NUN 07212 ONL and the Reference Variety (p=0.559) for plant height (cm) based on a trial in the US in 2021.

TABLE 7

| Statistical Parameter | Application Variety NUN 07212 ONL | Reference Variety NUN 07206 ON |
| --- | --- | --- |
| No. of samples | 15 | 15 |
| Minimum | 29.0 | 24.0 |
| Maximum | 38.0 | 38.50 |
| Median | 34.0 | 34.0 |
| Mean | 33.30 | 33.97 |
| Standard deviation | 2.97 | 3.20 |

Table 8 shows no significant difference at 5% significance level between onion variety NUN 07212 ONL and the Reference Variety (p=0.057) for pseudo stem length (mm) based on a trial in the US in 2021.

TABLE 8

| Statistical Parameter | Application Variety NUN 07212 ONL | Reference Variety NUN 07206 ON |
| --- | --- | --- |
| No. of samples | 15 | 15 |
| Minimum | 41.79 | 60.79 |
| Maximum | 78.42 | 89.10 |
| Median | 64.84 | 65.77 |
| Mean | 63.38 | 70.92 |
| Standard deviation | 11.05 | 9.76 |

The invention claimed is:

1. A plant or seed of variety NUN 07212 ONL, or a part thereof, wherein a representative sample of seed of said onion variety NUN 07212 ONL is deposited under Accession Number NCIMB 43755.

2. A plant part of the plant of claim 1, wherein the plant part is a leaf, a bulb, a scale, an umbel, or a cutting.

3. A plant or regenerable part thereof, produced by growing the seed of claim 1.

4. An onion plant or a part thereof having all of the physiological and morphological characteristics of the onion plant of claim 1 when grown under the same environmental conditions.

5. A tissue or cell culture of regenerable cells of the plant or plant part of claim 1.

6. The tissue or cell culture according to claim 5, comprising cells or protoplasts derived from a plant part of onion variety NUN 07212 ONL suitable for vegetative reproduction, wherein the plant part is a meristem, a cotyledon, a hypocotyl, a seed coat, a leaf, an anther, a bulb, a scale, an umbel, a pistil, a petiole, a flower, a fruit, a stem, or a stalk.

7. An onion plant regenerated from the tissue or cell culture of claim 5, wherein the plant has all of the physiological and morphological characteristics of onion variety NUN 07212 ONL when grown under the same environmental conditions, and wherein a representative sample of seed of said onion variety NUN 07212 ONL has been deposited under Accession Number NCIMB 43755.

8. A method of producing the plant of claim 1 or a part thereof, said method comprising vegetative propagation of at least a part of the plant of onion variety NUN 07212 ONL.

9. The method of claim 8, wherein said vegetative propagation comprises regenerating a whole plant from said part of onion variety NUN 07212 ONL, wherein a representative sample of seed of said onion variety NUN 07212 ONL has been deposited under Accession Number NCIMB 43755.

10. The method of claim 8, wherein said part is a bulb, cutting, a cell culture, or a tissue culture.

11. A vegetative propagated plant or part thereof produced by the method of claim 8, wherein the vegetative propagated plant or part thereof has all of the physiological and morphological characteristics of onion variety NUN 07212 ONL when grown under the same environmental conditions, and wherein a representative sample of seed of said onion variety NUN 07212 ONL has been deposited under Accession Number NCIMB 43755.

12. A method of producing an onion plant, said method comprising crossing the plant of claim 1 with a second onion plant at least once, and selecting a progeny onion plant from said crossing and optionally allowing the progeny to form seed, and wherein a representative sample of seed of onion variety NUN 07212 ONL has been deposited under Accession Number NCIMB 43755.

13. A method of producing an onion seed, said method comprising crossing onion plants and harvesting the resultant seed, wherein at least one onion plant in the cross is the plant of claim 1, wherein a representative sample of seed of said onion variety NUN 07212 ONL has been deposited under Accession Number NCIMB 43755.

14. A method of producing doubled haploids of the plant of claim 1, said method comprising making doubled haploid cells from haploid cells made from the plant or plant part of claim 1 by chromosome doubling, and wherein a representative sample of seed of said onion variety NUN 07212 ONL has been deposited under Accession Number NCIMB 43755.

15. A method of producing an onion bulb, said method comprising obtaining a plant according to claim 1, wherein the plant has been cultivated to maturity, and collecting the bulb from the plant.

16. An onion bulb produced by the method of claim 15.

17. A container comprising the onion bulb collected in the method of claim 15.

18. A container comprising the plant part of claim 2, wherein the plant part is a bulb or a part thereof.

19. A container comprising the seed of claim 1.

20. A food or a feed product comprising the plant part of claim 2, wherein the plant part is a bulb or a part thereof.

21. A method of introducing a desired trait into the plant of claim 1, said method comprising transforming the plant of claim 1 with a transgene that confers the desired trait, wherein the desired trait is male sterility, herbicide tolerance, insect resistance, pest resistance, disease resistance, environmental stress tolerance, modified carbohydrate metabolism, or modified protein metabolism.

22. An onion plant produced by the method of claim 21, wherein the plant contains the desired trait and otherwise has all of the physiological and morphological characteristics of onion variety NUN 07212 ONL.

23. A method of producing a modified onion plant having a desired trait, said method comprising mutating the onion plant of variety NUN 07212 ONL and selecting a mutated plant with the desired trait, wherein a representative sample of seed of said onion variety has been deposited under Accession Number NCIMB 43755.

24. A method for determining the genotype of the plant of claim 1, said method comprising obtaining a sample of nucleic acids from said plant, detecting in said nucleic acid a plurality of polymorphisms, thereby determining the genotype of the plant, and storing the results of detecting the plurality of polymorphisms on a computer readable medium.

25. A method for developing an onion plant in an onion breeding program, said method consisting applying plant breeding techniques comprising recurrent selection, backcrossing, mass selection, mutation breeding, genetic marker enhanced selection, or genetic transformation to the plant of claim 1 or part thereof, wherein said plant breeding techniques result in a development of an onion plant.

26. A method of producing an onion plant derived from the plant of claim 1, comprising:
   a. preparing a progeny onion plant derived from onion variety NUN 07212 ONL by crossing the plant of claim 1 with itself or with a second onion plant, wherein a representative sample of seed of said onion variety has been deposited under Accession Number NCIMB 43755;
   b. crossing the progeny plant with itself or a second onion plant to produce seed of a progeny plant of the subsequent generation;
   c. growing a progeny plant of the subsequent generation from said seed and crossing the progeny plant of the subsequent generation with itself or a second onion plant;
   d. repeating steps (b) and (c) for at least one more generation to produce an onion plant derived from onion variety NUN 07212 ONL.

* * * * *